(12) United States Patent
Fan et al.

(10) Patent No.: US 8,361,965 B2
(45) Date of Patent: Jan. 29, 2013

(54) RECOMBINANT CHIMERIC PROTEIN OF NEUTROPHIL INHIBITORY FACTOR AND HIRUGEN, AND PHARMACEUTICAL COMPOSITION THEREOF

(75) Inventors: Kai Fan, Chongqing (CN); Zhiquan Zhao, Linyi (CN)

(73) Assignees: Lunan Pharmaceutical Group Corporation, Linyi (CN); Fagen Biomedical Inc. Chongqing, Chongqing (CN)

( * ) Notice: Subject to any disclaimer, the term of this patent is extended or adjusted under 35 U.S.C. 154(b) by 177 days.

(21) Appl. No.: 12/526,692

(22) PCT Filed: Feb. 18, 2008

(86) PCT No.: PCT/CN2008/000359
§ 371 (c)(1),
(2), (4) Date: Aug. 11, 2009

(87) PCT Pub. No.: WO2008/101415
PCT Pub. Date: Aug. 28, 2008

(65) Prior Publication Data
US 2010/0150860 A1  Jun. 17, 2010

(51) Int. Cl.
*A61K 38/58* (2006.01)
*C07K 14/815* (2006.01)
(52) U.S. Cl. ........................ 514/14.8; 930/210; 530/350
(58) Field of Classification Search .................... None
See application file for complete search history.

(56) References Cited

U.S. PATENT DOCUMENTS

| 5,632,991 A * | 5/1997 | Gimbrone, Jr. ............ 424/178.1 |
| 5,789,175 A | 8/1998 | Priest |
| 6,818,616 B1 * | 11/2004 | Moyle et al. .................... 514/2.4 |
| 2002/0122798 A1 * | 9/2002 | Young ........................ 424/141.1 |

FOREIGN PATENT DOCUMENTS

CN  1517365  *  8/2004

OTHER PUBLICATIONS

Alving et al. Newer antithrombotic agents: Potential for clinical use in venous and arterial thrombosis. J Thromb Thrombolysis. 1996;2(4): 285-288.*
Bowie et al. Deciphering the message in protein sequences: tolerance to amino acid substitutions. Science, (Mar. 16, 1990) 247 (4948) 1306-10.*
Guo et al. Protein tolerance to random amino acid change. Proc Natl Acad Sci U S A. Jun. 22, 2004;101(25):9205-10. Epub Jun. 14, 2004.*
Machine translation of CN 1517365. Retrieved from the Internet:<URL:http://cs.dialog.com/client/csc_sh127/>. Retrieved on Sep. 7, 2011.*
Ngo et al., in The Protein Folding Problem and Tertiary Structure Prediction, Merz and Le Grand (Eds), Aug. 1994, Springer Verlag, pp. 433 and 492-495.*
Sherman et al. Methionine or not methionine at the beginning of a protein. Bioessays. Jul. 1985;3(1):27-31.*
Madden et al., "A Peptide Derived from Neutrophil Inhibitory Factor (NIF) Blocks Neutrophil Adherence to Endothelial Cells." Inflammation Research, vol. 46, pp. 216-223 (1997).
Maraganore et al., "Design and Characterization of Hirulogs: a Novel Class of Bivalent Peptide Inhibitors of Thrombin." Biochemistry, vol. 29, pp. 7095-7101 (1990).
Moyle et al., "A Hookworm Glycoprotein That Inhibits Neutrophil Function Is a Ligand of the Integrin CD11b/CD18." The Journal of Biological Chemistry, vol. 269, No. 13, pp. 10008-10015 (1994).
Zhang et al., "Effects of a Selective CD11b/Cd18 Antagonist and Recombinant Human Tissue Plasminogen Activator Treatment Alone and in Combination in a Rat Embolic Model of Stroke." Journal of the American Heart Association, vol. 34, pp. 1790-1795 (2003).

* cited by examiner

*Primary Examiner* — David Romeo
(74) *Attorney, Agent, or Firm* — Occhiuti Rohlicek & Tsao LLP

(57) ABSTRACT

A chimeric protein containing neutrophil inhibitory factor and hirugen, the chimeric protein having an amino acid sequence that includes FPRPGSGG (SEQ ID NO:21) Also provided is a pharmaceutical composition comprising the chimeric protein, which can be used for treating or preventing cerebral injury and cerebral edema, or for inhibiting platelet aggregation.

17 Claims, 6 Drawing Sheets

US 8,361,965 B2

Figure 1:
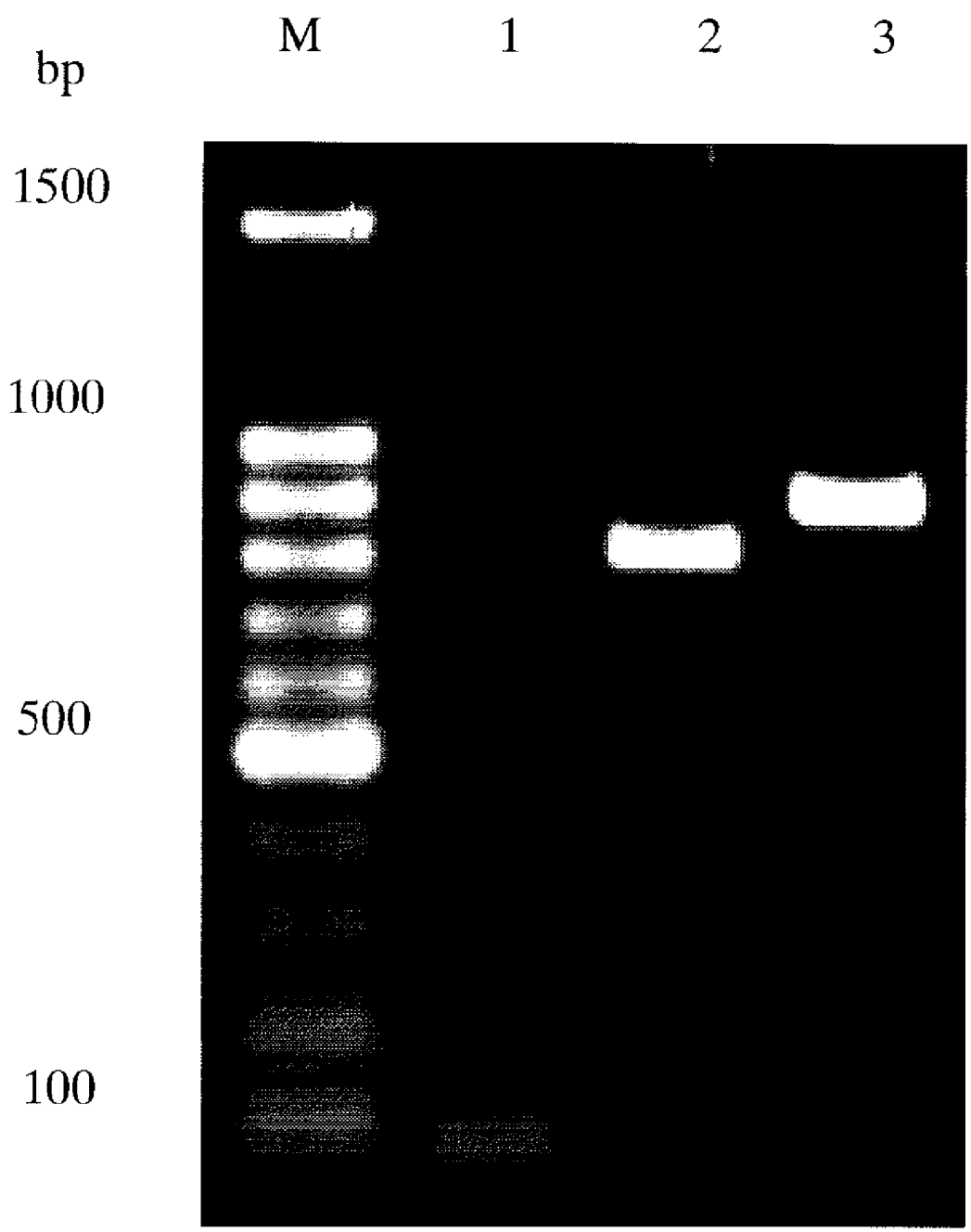

```
                        SEQUENCE LISTING

<160> NUMBER OF SEQ ID NOS: 21

<210> SEQ ID NO 1
<211> LENGTH: 846
<212> TYPE: DNA
<213> ORGANISM: Artificial sequence
<220> FEATURE:
<223> OTHER INFORMATION: Synthetic polynucleotide

<400> SEQUENCE: 1
ctcgagaaaa gaaacgaaca caacttgaga tgtccacaaa acggtactga aatgccaggt      60
ttcaacgact ccatcagatt gcaattcttg gctatgcaca acggttacag atccaagttg     120
gctttgggtc acatctccat cactgaagaa tccgaatccg acgacgacga cgacttcggt     180
ttcttgccag acttcgctcc aagagcttcc aagatgagat acttggaata cgactgtgaa     240
gctgaaaagt ccgcttacat gtccgctaga aactgttccg actcctcctc cccaccagaa     300
ggttacgacg aaaacaagta catcttcgaa aactccaaca acatctccga agctgctttg     360
aaggctatga tctcctgggc taaggaagct ttcaacttga acaagactaa ggaaggtgaa     420
ggtgttttgt acagatccaa ccacgacatc tccaacttcg ctaacttggc ttgggacgct     480
agagaaaagt tcggttgtgc tgttgttaac tgtccattgg gtgaaatcga cgacgaaact     540
aaccacgacg gtgaaactta cgctactact atccacgttg tttgtcacta cccaaagatc     600
```

```
aacaagactg aaggtcaacc aatctacaag gttggtactc catgtgacga ctgttccgaa     660
tacactaaga aggctgacaa cactacttcc gctgacccag tttgtatccc agacgacggt     720
gtttgtttca tcggttccaa ggctgactac gactccaagg agttctacag attcagagaa     780
ttgggcggtg gcggtggcaa cggtgacttc gaagaaatcc agaagaata cttgtaatga     840 tctaga                                                                846
```

<210> SEQ ID NO 2
<211> LENGTH: 846
<212> TYPE: DNA
<213> ORGANISM: Artificial sequence
<220> FEATURE:
<223> OTHER INFORMATION: Synthetic polynucleotide

<400> SEQUENCE: 2

```
aacgaacaca acttgagatg tccacaaaac ggtactgaaa tgccaggttt caacgactcc      60
atcagattgc aattcttggc tatgcacaac ggttacagat ccaagttggc tttgggtcac     120
atctccatca ctgaagaatc cgaatccgac gacgacgacg acttcggttt cttgccagac     180
ttcgctccaa gagcttccaa gatgagatac ttggaatacg actgtgaagc tgaaaagtcc     240
gcttacatgt ccgctagaaa ctgttccgac tcctcctccc caccagaagg ttacgacgaa     300
aacaagtaca tcttcgaaaa ctccaacaac atctccgaag ctgctttgaa ggctatgatc     360
tcctgggcta aggaagcttt caacttgaac aagactaagg aaggtgaagg tgttttgtac     420
agatccaacc acgacatctc caacttcgct aacttggctt gggacgctag agaaaagttc     480
ggttgtgctg ttgttaactg tccattgggt gaaatcgacg acgaaactaa ccacgacggt     540
gaaacttacg ctactactat ccacgttgtt tgtcactacc aaagatcaa caagactgaa     600 ggtcaaccaa tctacaaggt tggtactcca tgtgacgact gttccgaata cactaagaag     660
gctgacaaca ctacttccgc tgacccagtt tgtatcccag acgacggtgt tgtttcatc     720 ggttccaagg ctgactacga ctccaaggag ttctacagat cagagaatt gggcggtggc     780 ggtggcttcc aagaccagg tagcggtggc aacggtgact cgaagaaat cccagaagaa     840 tacttg                                                                846
```

<210> SEQ ID NO 3
<211> LENGTH: 283
<212> TYPE: PRT
<213> ORGANISM: Artificial sequence
<220> FEATURE:
<223> OTHER INFORMATION: Synthetic polypeptide

<400> SEQUENCE: 3

```
Met Asn Glu His Asn Leu Arg Cys Pro Gln Asn Gly Thr Glu Met Pro
1               5                   10                  15

Gly Phe Asn Asp Ser Ile Arg Leu Gln Phe Leu Ala Met His Asn Gly
            20                  25                  30

Tyr Arg Ser Lys Leu Ala Leu Gly His Ile Ser Ile Thr Glu Glu Ser
        35                  40                  45

Glu Ser Asp Asp Asp Asp Asp Phe Gly Phe Leu Pro Asp Phe Ala Pro
    50                  55                  60

Arg Ala Ser Lys Met Arg Tyr Leu Glu Tyr Asp Cys Glu Ala Glu Lys
65                  70                  75                  80

Ser Ala Tyr Met Ser Ala Arg Asn Cys Ser Asp Ser Ser Pro Pro
            85                  90                  95

Glu Gly Tyr Asp Glu Asn Lys Tyr Ile Phe Glu Asn Ser Asn Asn Ile
            100                 105                 110
```

-continued

```
Ser Glu Ala Ala Leu Lys Ala Met Ile Ser Trp Ala Lys Glu Ala Phe
        115                 120                 125

Asn Leu Asn Lys Thr Lys Glu Gly Glu Gly Val Leu Tyr Arg Ser Asn
    130                 135                 140

His Asp Ile Ser Asn Phe Ala Asn Leu Ala Trp Asp Ala Arg Glu Lys
145                 150                 155                 160

Phe Gly Cys Ala Val Val Asn Cys Pro Leu Gly Glu Ile Asp Asp Glu
                165                 170                 175

Thr Asn His Asp Gly Glu Thr Tyr Ala Thr Thr Ile His Val Val Cys
            180                 185                 190

His Tyr Pro Lys Ile Asn Lys Thr Glu Gly Gln Pro Ile Tyr Lys Val
        195                 200                 205

Gly Thr Pro Cys Asp Asp Cys Ser Glu Tyr Thr Lys Lys Ala Asp Asn
    210                 215                 220

Thr Thr Ser Ala Asp Pro Val Cys Ile Pro Asp Asp Gly Val Cys Phe
225                 230                 235                 240

Ile Gly Ser Lys Ala Asp Tyr Asp Ser Lys Glu Phe Tyr Arg Phe Arg
                245                 250                 255

Glu Leu Gly Gly Gly Gly Phe Pro Arg Pro Gly Ser Gly Gly Asn
            260                 265                 270

Gly Asp Phe Glu Glu Ile Pro Glu Glu Tyr Leu
        275                 280
```

<210> SEQ ID NO 4
<211> LENGTH: 32
<212> TYPE: DNA
<213> ORGANISM: Artificial sequence
<220> FEATURE:
<223> OTHER INFORMATION: Oligonucleotide

<400> SEQUENCE: 4
cgcatatgaa cgaacacaac ttgagatgtc ca         32

<210> SEQ ID NO 5
<211> LENGTH: 42
<212> TYPE: DNA
<213> ORGANISM: Artificial sequence
<220> FEATURE:
<223> OTHER INFORMATION: Oligonucleotide

<400> SEQUENCE: 5
acctggtctt gggaagccac cgccaccgcc caattctctg aa         42

<210> SEQ ID NO 6
<211> LENGTH: 39
<212> TYPE: DNA
<213> ORGANISM: Artificial sequence
<220> FEATURE:
<223> OTHER INFORMATION: Oligonucleotide

<400> SEQUENCE: 6
ggcttcccaa gaccaggtag cggtggcaac ggtgacttc         39

<210> SEQ ID NO 7
<211> LENGTH: 32
<212> TYPE: DNA
<213> ORGANISM: Artificial sequence
<220> FEATURE:
<223> OTHER INFORMATION: Oligonucleotide

<400> SEQUENCE: 7

```
tgggatccttt acaagtattc ttctgggatt tc                                      32
```

<210> SEQ ID NO 8
<211> LENGTH: 72
<212> TYPE: DNA
<213> ORGANISM: Artificial sequence
<220> FEATURE:
<223> OTHER INFORMATION: Oligonucleotide

<400> SEQUENCE: 8

```
acctggtctt gggaagccac cgccaccgcc accgccaccg ccaccgccac cgccaccgcc        60
caattctctg aa                                                             72
```

<210> SEQ ID NO 9
<211> LENGTH: 63
<212> TYPE: DNA
<213> ORGANISM: Artificial sequence
<220> FEATURE:
<223> OTHER INFORMATION: Oligonucleotide

<400> SEQUENCE: 9

```
ggcttcccaa gaccaggtag cggtggcggt agcggtggcg gtagcggtgg caacggtgac        60
ttc                                                                       63
```

<210> SEQ ID NO 10
<211> LENGTH: 5
<212> TYPE: PRT
<213> ORGANISM: Artificial sequence
<220> FEATURE:
<223> OTHER INFORMATION: Pentapeptide

<400> SEQUENCE: 10

Gly Gly Gly Gly Gly
1               5

<210> SEQ ID NO 11
<211> LENGTH: 4
<212> TYPE: PRT
<213> ORGANISM: Artificial sequence
<220> FEATURE:
<223> OTHER INFORMATION: Tetrapeptide

<400> SEQUENCE: 11

Phe Pro Arg Pro
1

<210> SEQ ID NO 12
<211> LENGTH: 4
<212> TYPE: PRT
<213> ORGANISM: Artificial sequence
<220> FEATURE:
<223> OTHER INFORMATION: Tetrapeptide

<400> SEQUENCE: 12

Gly Ser Gly Gly
1

<210> SEQ ID NO 13
<211> LENGTH: 8
<212> TYPE: PRT
<213> ORGANISM: Artificial sequence
<220> FEATURE:
<223> OTHER INFORMATION: Octapeptide

<400> SEQUENCE: 13

Gly Ser Gly Gly Gly Ser Gly Gly

```
<210> SEQ ID NO 14
<211> LENGTH: 12
<212> TYPE: PRT
<213> ORGANISM: Artificial sequence
<220> FEATURE:
<223> OTHER INFORMATION: Dodecapeptide

<400> SEQUENCE: 14

Gly Ser Gly Gly Gly Ser Gly Gly Gly Ser Gly Gly
1               5                   10

<210> SEQ ID NO 15
<211> LENGTH: 13
<212> TYPE: PRT
<213> ORGANISM: Artificial sequence
<220> FEATURE:
<223> OTHER INFORMATION: Tridecapeptide

<400> SEQUENCE: 15

Gly Gly Gly Gly Gly Phe Pro Arg Pro Gly Ser Gly Gly
1               5                   10

<210> SEQ ID NO 16
<211> LENGTH: 15
<212> TYPE: PRT
<213> ORGANISM: Artificial sequence
<220> FEATURE:
<223> OTHER INFORMATION: Pentadecapeptide

<400> SEQUENCE: 16

Met Asn Glu His Asn Leu Arg Cys Pro Gln Asn Gly Thr Glu Met
1               5                   10                  15

<210> SEQ ID NO 17
<211> LENGTH: 12
<212> TYPE: PRT
<213> ORGANISM: Artificial sequence
<220> FEATURE:
<223> OTHER INFORMATION: Dodecapeptide

<400> SEQUENCE: 17

Asn Gly Asp Phe Glu Glu Ile Pro Glu Glu Tyr Leu
1               5                   10

<210> SEQ ID NO 18
<211> LENGTH: 15
<212> TYPE: PRT
<213> ORGANISM: Artificial sequence
<220> FEATURE:
<223> OTHER INFORMATION: Pentadecapeptide

<400> SEQUENCE: 18

Gly Gly Gly Gly Gly Gly Gly Gly Gly Gly Gly Gly Gly Gly Gly
1               5                   10                  15

<210> SEQ ID NO 19
<211> LENGTH: 31
<212> TYPE: PRT
<213> ORGANISM: Artificial sequence
<220> FEATURE:
<223> OTHER INFORMATION: Hentriacontapeptide

<400> SEQUENCE: 19

Gly Gly Gly Gly Gly Gly Gly Gly Gly Gly Gly Gly Gly Gly Phe
1               5                   10                  15
```

```
Pro Arg Pro Gly Ser Gly Gly Gly Ser Gly Gly Ser Gly Gly
            20                  25                  30

<210> SEQ ID NO 20
<211> LENGTH: 9
<212> TYPE: PRT
<213> ORGANISM: Artificial sequence
<220> FEATURE:
<223> OTHER INFORMATION: Enneapeptide

<400> SEQUENCE: 20

Asp Phe Pro Arg Pro Gly Gly Gly Gly
1               5

<210> SEQ ID NO 21
<211> LENGTH: 8
<212> TYPE: PRT
<213> ORGANISM: Artificial sequence
<220> FEATURE:
<223> OTHER INFORMATION: Octapeptide

<400> SEQUENCE: 21

Phe Pro Arg Pro Gly Ser Gly Gly
1               5
```

RECOMBINANT CHIMERIC PROTEIN OF NEUTROPHIL INHIBITORY FACTOR AND HIRUGEN, AND PHARMACEUTICAL COMPOSITION THEREOF

CROSS-REFERENCE TO RELATED APPLICATIONS

This application is the National Stage of International Application No. PCT/CN2008/000359 filed Feb. 18, 2008 which claims the priority of Chinese Application No. 200710084133.1, filed on Feb. 16, 2007. The contents of both applications are hereby incorporated by reference in their entirety.

TECHNICAL FIELD

The invention relates to a recombinant chimeric protein of neutrophil inhibitory factor and hirugen (TNHH), a polynucleotide sequence encoding the same, a recombinant vector comprising the polynucleotide sequence, a microorganism transformed by the vector, and a pharmaceutical composition comprising the recombinant chimeric protein of neutrophil inhibitory factor and hirugen.

BACKGROUND OF THE INVENTION

Nowadays, cardio-cerebrovascular disease is one of the main diseases threatening human health, among which brain stroke leads to an extraordinarily high mortality rate. The main pathological symptoms thereof include: (1) the formation of cerebral hematoma, (2) cerebral thrombosis, (3) cerebral ischemia, and (4) the occurrence of cerebral edema. At present, above pathological symptoms are considered to be associated with leukocyte infiltration, thrombin activation and microcirculation disorders. It is known that neutrophil inhibitory factor and hirudin can inhibit leukocyte infiltration and thrombin activation, respectively (Moyle M et al: U.S. Pat. No. 5,789,175; Madden K et al, Inflamm Res 1997, 46(6): 216-223; Masadda T. et al, Brain Res, 2000, 867(2):173-179.). Neutrophil inhibitory factor (NIF) consists of 257 amino acids and contains seven glycosylation sites. It has been proved that recombinant deglycosylated NIF retains the biological activities. NIF can effectively inhibit neutrophil activities including adhesion to endothelial cells, release of hydrogen peroxide and superoxide ions, as well as chemotaxis, aggregation and phagocytosis of neutrophil, etc (Moyle M et al: J Biol chem 1994, 269(13):10008-10015). In view of the above efficacies of NIF, it is demonstrated in the animal model that recombinant NIF has clinical values on preventing and treating ischemic neural injury (rat MCAO model), improving blood supply during brain injury, and alleviating brain tissue injury area (Zhang L et al: stroke. 2003, 34(7): 1790-1795).

It is found that the C-terminal dodecapeptide (i.e. $53^{rd}$-$64^{th}$ amino acids) of the hirudin possesses all the functions as hirudin antithrombin activities by investigating the structure and function of hirudin (Naski M C. et al: J Biocchem. 1990, 265(23):13484-13489; Maraganore J metal: Biochemistry. 1990, 29(30):7095-7101). An artificial dodecapeptide is synthesized artificially based on above results, denominated as hirugen. It is proved that hirugen can bind to the anion-binding region of thrombin, but can not bind to the catalytic site region and fibrin. Thrombin can bind to fibrin, so hirugen can not specifically bind to thrombin, i.e., hirugen can not target to thrombin. However, hirugen can inhibit thrombin both in vivo and in vitro to convert fibrinogen to fibrin, and elongate APTT, PT and TT, thus achieving anticoagulation effect.

Upon above pathological studies and biological activities of NIF and hirugen, Chinese patent application (Application No. 031011551) discloses a bifunctional chimeric protein (NIF-hirudin hybrid, or NHH for short) derived from NIF and hirugen by genetic recombination technique. The chimeric protein is represented as NIF-$(Gly)_5$ (SEQ ID No: 10)-hirugen. The NHH consists of 274 amino acids, and possesses the functions of inhibiting the adhesion and activation of neutrophil, as well as inhibiting thrombin activity, thus being suitable for treating acute cerebrovascular diseases. Unfortunately, since the hirugen contained in the NHH can not bind to the catalytic site region, the NHH can not target to thrombin, which greatly decreases the therapeutic efficacy of NHH on cardio-cerebrovascular disease.

SUMMARY OF THE INVENTION

To overcome the disadvantages in the prior art, the invention aims to provide a novel recombinant chimeric protein of neutrophil inhibitory factor and hirugen, capable of targeting inhibition of thrombin activity, thus improving the therapeutic efficacy in the treatment of cardio-cerebrovascular disease, such as brain stroke.

For achieving above purposes, the invention in the first aspect provides a recombinant chimeric protein of neutrophil inhibitory factor and hirugen (TNHH) with the following structure: Met-NIF-linker 1-FPRP (SEQ ID No: 11)-linker 2-hirugen, or NIF-linker 1-FPRP (SEQ ID No: 11)-linker 2-hirugen. Preferably, the linker 1 is 5-15 glycines, and more preferably is 5-10 glycines; and the linker 2 is $(GSGG)_n$, n=1-3 (SEQ ID No: 12-14).

In the second aspect, the invention provides a polynucleotide sequence encoding the recombinant chimeric protein of neutrophil inhibitory factor and hirugen.

In the third aspect, the invention provides an expression vector comprising the polynucleotide sequence.

In the fourth aspect, the invention provides a microorganism comprising the expression vector.

In the fifth aspect, the invention provides a pharmaceutical composition comprising the recombinant chimeric protein of neutrophil inhibitory factor and hirugen.

The TNHH according to this invention has the structure of: Met-NIF-linker 1-FPRP (SEQ ID No: 11)-linker 2-hirugen, or NIF-linker 1-FPRP (SEQ ID No: 11)-linker 2-hirugen. Preferably, linker 1 of TNHH is 5-15 glycines, more preferably 5-10 glycines; and the linker 2 is $(GSGG)_n$, wherein n=1-3 (SEQ ID No: 12-14), more preferably n=1. Within the FPRP (SEQ ID No: 11), phenylalanine (F) is preferably in L-form; and Met stands for methionine. Preferably, the chimeric protein is Met-NIF(257)-$(Gly)_5$-FPRPGSGG (SEQ ID No: 15)-Hirugen, wherein phenylalanine (F) in the FPRP (SEQ ID No: 11) is in L-form.

The TNHH according to this invention also includes an amino acid sequence sharing about 80% or more, preferably 90% or more identity with the amino acid sequence of Met-NIF-linker 1-FPRP (SEQ ID No: 11)-linker 2-hirugen, or NIF-linker 1-FPRP (SEQ ID No: 11)-linker 2-hirugen, and having therapeutic activity for cardio-cerebrovascular disease, such as brain stroke. Typically, a higher value is preferred for the identity value. The identity of the amino acid sequences can be determined by the BLAST Algorithm of Karlin and Altschul (Proc. Natl. Acad. Sci. USA 87: 2264-2268, 1990; Proc. Natl. Acad. Sci. USA 90:5873, 1993).

The FPRP (SEQ ID No: 11) structure within TNHH can specifically bind to fibrin, rendering TNHH targeting for inhibition of thrombin activity and treatment of cardio-cerebrovascular disease.

Figure 10:
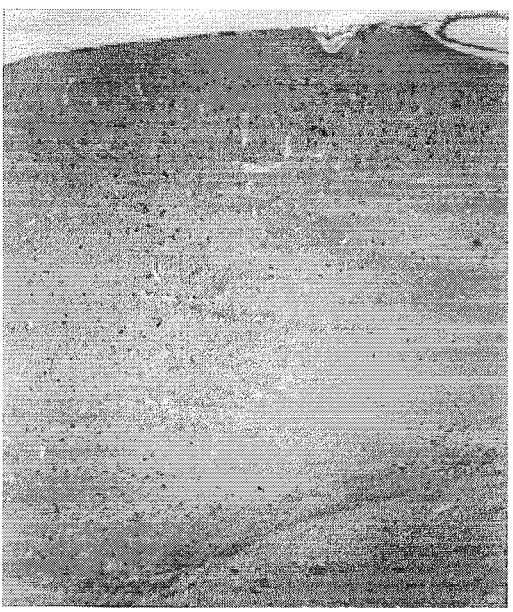

Furthermore, the TNHH according to this invention has an excellent behavior on treating or preventing cardio-cerebrovascular disease, such as treating or preventing brain ischemic injury or cerebral hematoma, and has a notable progress on inhibiting platelet aggregation or inhibiting peripheral leukocyte activation. The cardio-cerebrovascular disease is preferably brain stroke.

To prepare TNHH, the invention takes following steps: (1) designing a cDNA sequence corresponding to NHH to be artificially synthesized, based on the cDNA of NIF from GenBank and the codon sequence deduced from the hirugen dodecapeptide, in combination with the preferable codons of *Escherichia coli*, yeast or CHO, (2) designing plural pairs of complementary over-lapped primers based on above-designed cDNA sequence, amplifying the cDNA sequence by a recursive PCR, inserting the amplified product into the sequencing plasmid pUC57, and sequencing with an automatic DNA sequencer (ABI) for ensuring the identity between the designed cDNA sequence and the artificially synthesized cDNA sequence, (3) designing primers by use of pUC57 comprising the base sequence designed in step (2) as a template for amplifying TNHH gene, and in the amplified gene, the front region and the terminal region comprise cleavage sites, respectively, and the terminal region additionally comprises a terminator, preferably a TAATGA terminator, in the front of the cleavage site, for conveniently inserting the amplified gene into an expression vector and expressing the expression vector in host cells; the cleavage sites of Nde I and BanH I are respectively preferred in the front region and the terminal region for conveniently inserting the amplified gene into prokaryotic expression vector pET-3c, (4) using a sequencing plasmid with the same cleavage sites as the amplified TNHH gene for detecting the identity between the designed sequence and the amplified TNHH gene, as the amplified TNHH gene comprise cleavage sites in the front region and the terminal region, subsequently cleaving the sequencing plasmid comprising the correct TNHH gene and an expression vector, and ligating the correct TNHH gene to the expression vector to obtain the expression vector comprising TNHH gene, and (5) transforming a host cell with the expression vector comprising TNHH gene, performing sequencing analysis on the transformant host cell for ensuring the correct insertion of TNHH gene and identity between the designed sequence and the target gene sequence, expressing the TNHH protein in the host cell, and extracting and purifying the TNHH protein from the host cell. The TNHH protein sequence consists of NIF, linkers and hirugen, wherein the NIF sequence is located at N-terminal and consists of 274 amino acids. According to examples 1-7, the expression vector for preparing recombinant TNHH is PET system expressed in *E. coli*. When expressing in prokaryotic organisms, the start codon ATG at the 5'-terminal of the recombinant TNHH is translated into methionine (Met). Thus, the recombinant TNHH product expressed by *E. coli* is met-TNHH. When the same TNHH polynucleotide sequence is expressed in eukaryotic expression systems, such as yeast, mammalian cell (CHO) and like, the recombinant TNHH product is free of Met at N-terminal. In this invention, the biological effects and pharmacodynamic efficacies of TNHH are independent of Met at the N terminal of the recombinant TNHH product obtained by expressing the amino acid sequence of TNHH according to this invention in prokaryotic or eukaryotic organisms.

The invention also provides polynucleotide sequences encoding the recombinant chimeric protein of neutrophil inhibitory factor and hirugen, among which the polynucleotide of SEQ ID NO: 2 is preferred.

Preferably, the expression vector comprising the polynucleotide according to present invention is pET system.

The host cells comprising the expression vector according to present invention include *E. coli*, yeast cell, and CHO cells, etc., among which *E. coli* is preferred.

The pharmaceutical composition according to present invention can be any conventional dosage forms administrated by any conventional delivery routes, among which parenteral administration is preferred. The preferable dosage form is injection formulation, including injection solution, lyophilized powder for injecting, etc. When preparing the injection formulation, the TNHH according to present invention is added to a certain amount of an inorganic salt or an amino acid buffer, such as phosphate, acetate, carbonate, citrate, glycine, histidine, wherein the salt is preferably sodium salt, and the ionic strength thereof is in the range of 5-100 mmol/L. The pH value of the pharmaceutical composition is in the range of 5.0-9.0. A protein protector, such as albumin, gelatin, polysaccharide, starch, glycerol and the like, can also be added into the composition, wherein the polysaccharide is selected from one or more of mannitol, sucrose and trehalose to a concentration (g/ml) of 2.0-6.0%.

The pharmaceutical composition comprising TNHH according to present invention can be used for treating cardio-cerebrovascular disease, especially brain stroke.

BRIEF DESCRIPTION OF THE FIGURES

FIG. 1: DNA fragments amplified by PCR, wherein, M: 100 bp DNA Ladder Marker; 1: Hirulog gene (70 bp); 2: NIF gene (810 bp); 3: TNHH gene (870 bp)

FIG. 2: Identification of pLEX-TNHH, pLEX and pET3c plasmids by enzymatic digestion, wherein, M1: λDNA/Hind III+EcoR I digest; 1: pLEX-TNHH/Nde I+BamH I; 2: pLEX/Nde I+BamH I; 3: pET3c/Nde I+BamH I; M2: 100 bp DNA Ladder Marker FIG. 3: Construction of recombinant expression plasmid pET3-TNHH FIG. 4: Identification of recombinant plasmid pET3-TNHH, wherein, M: λDNA/HindIII+EcoRI digest; 1: pET3c/Nde I+BamH I; 2-3: pET3-TNHH/Nde I+BamH I; 4: PCR fragment of TNHH gene FIG. 5: Immunoblotting identification of TNHH, wherein, M: protein molecular weight marker; 1: purified TNHH; 2: Hirudin; 1': Immunoblotting of TNHH; 2': the Immunoblotting of Hirudin FIG. 6: In the normal control group, the nerve cells in the cerebral cortex had regular arrangements, deeply stained nucleus, cytoplasmic shrinkage or disappearance FIG. 7: In the model group, the nerve cells in the cerebral cortex had irregular arrangements, deeply stained nuclears, and cytoplasmic shrinkage or disappearance FIG. 8: In the NIF group, the nerve cells in the cerebral cortex had less regular arrangements, a portion of deeply stained nucleus, and some cytoplasmic shrinkage or disappearance FIG. 9: In the NHH group, the nerve cells in the cerebral cortex had less regular arrangements, a portion of deeply stained nucleus, and some cytoplasmic shrinkage or disappearance FIG. 10: In the TNHH group, the nerve cells in the cerebral cortex had more regular arrangements, a portion of deeply stained nucleus, and some cytoplasmic shrinkage or disappearance (HE 10×10)

Figure 11:
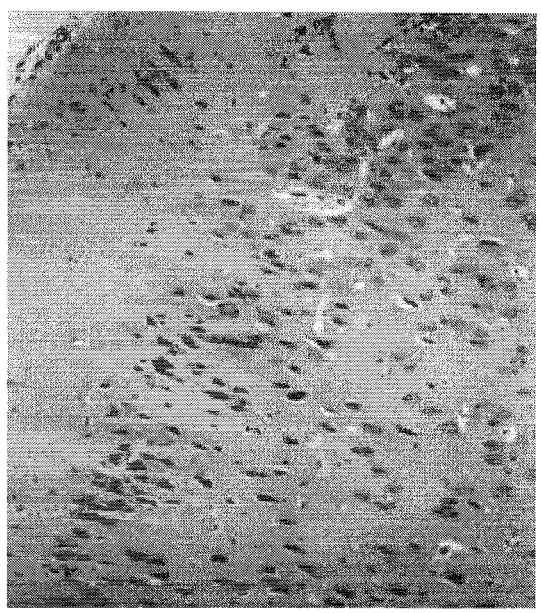

FIG. 11: In the TNHH group, the nerve cells in the cerebral cortex had more regular structural arrangements, a portion of deeply stained nucleus, and some cytoplasmic shrinkage or disappearance (HE 40×40)

DETAILED DESCRIPTION OF THE INVENTION

The present invention is illustrated by the following specific examples. However, the scope of present invention is not limited by these examples.

Example 1

Preparation of NHH Gene

The whole gene was artificially synthesized by Shanghai Sangon Biological Engineering Technology & Services Co., Ltd., and the design scheme thereof was as the follows:

14 oligonucleotide fragments with a length between 80 and 130 bps were synthesized based on the full length gene sequence of NHH (SEQ ID No: 1). The fragments Nos. 1, 3, 5, 7, 9, 11 and 13 were forward fragments, and the fragments Nos. 2, 4, 6, 8, 10, 12 and 14 were reverse fragments. A complementary region of about 20 bp was designed between two contiguous fragments. The above fragments were synthesized, purified and mixed in equivalent amounts as a substrate for recursive PCR. NHH gene of 822 bps is then obtained by PCR.

A Kex2 site was added in front of the NHH gene, and the first 6 bps of Kex2 site was an Xho I site; NHH gene was followed by two stop codons; and the stop codons were followed by an Xba I site.

The full length sequence of synthesized NHH gene is shown as the following (SEQ ID NO: 1):

```
CTC GAG AAA AGA AAC GAA CAC AAC TTG AGA TGT CCA CAA
        Kex2
 Xho
AAC GGT ACT GAA ATG CCA GGT TTC AAC GAC TCC ATC AGA TTG CAA
TTC TTG GCT ATG CAC AAC GGT TAC AGA TCC AAG TTG GCT TTG GGT CAC
ATC TCC ATC ACT GAA GAA TCC GAA TCC GAC GAC GAC GAC GAC TTC
GGT TTC TTG CCA GAC TTC GCT CCA AGA GCT TCC AAG ATG AGA TAC TTG
GAA TAC GAC TGT GAA GCT GAA AAG TCC GCT TAC ATG TCC GCT AGA AAC
TGT TCC GAC TCC TCC TCC CCA CCA GAA GGT TAC GAC GAA AAC AAG TAC
ATC TTC GAA AAC TCC AAC AAC ATC TCC GAA GCT GCT TTG AAG GCT ATG
ATC TCC TGG GCT AAG GAA GCT TTC AAC TTG AAC AAG ACT AAG GAA
GGT GAA GGT GTT TTG TAC AGA TCC AAC CAC GAC ATC TCC AAC TTC GCT
AAC TTG GCT TGG GAC GCT AGA GAA AAG TTC GGT TGT GCT GTT GTT
AAC TGT CCA TTG GGT GAA ATC GAC GAC GAA ACT AAC CAC GAC GGT
GAA ACT TAC GCT ACT ACT ATC CAC GTT GTT TGT CAC TAC CCA AAG ATC
AAC AAG ACT GAA GGT CAA CCA ATC TAC AAG GTT GGT ACT CCA TGT GAC
GAC TGT TCC GAA TAC ACT AAG AAG GCT GAC AAC ACT ACT TCC GCT
GAC CCA GTT TGT ATC CCA GAC GAC GGT GTT TGT TTC ATC GGT TCC AAG
GCT GAC TAC GAC TCC AAG GAG TTC TAC AGA TTC AGA GAA TTG GGC GGT GGC
GGT GGC GGT GGC AAC GGT GAC TTC GAA GAA ATC CCA GAA GAA TAC
TTG TAA TGA TCT AGA
        terminator   Xba I
```

The synthesized gene was inserted into plasmid pUC57, which was denominated as pUC57-NHH. The NHH gene was recombined with pPIC9K to construct a recombinant plasmid, which was then linearized and transformed into *Pichia pastoris*. Inductive expression was performed for preparing recombinant NHH as a control protein for the animal model.

Example 2

Preparation of TNHH Gene

In this example, the designed TNHH had a structure of Met-NIF-GGGGG-FPRPGSGG (SEQ ID No: 15)-hirugen, which corresponded to the polynucleotide sequence as the follows (SEQ ID NO: 2):

```
AAC GAA CAC AAC TTG AGA TGT CCA CAA AAC GGT ACT
GAA ATG CCA GGT TTC AAC GAC TCC ATC AGA TTG CAA
TTC TTG GCT ATG CAC AAC GGT TAC AGA TCC AAG TTG
GCT TTG GGT CAC ATC TCC ATC ACT GAA GAA TCC GAA
TCC GAC GAC GAC GAC GAC TTC GGT TTC TTG CCA GAC
TTC GCT CCA AGA GCT TCC AAG ATG AGA TAC TTG GAA
TAC GAC TGT GAA GCT GAA AAG TCC GCT TAC ATG TCC
GCT AGA AAC TGT TCC GAC TCC TCC TCC CCA CCA GAA
GGT TAC GAC GAA AAC AAG TAC ATC TTC GAA AAC TCC
AAC AAC ATC TCC GAA GCT GCT TTG AAG GCT ATG ATC
TCC TGG GCT AAG GAA GCT TTC AAC TTG AAC AAG ACT
AAG GAA GGT GAA GGT GTT TTG TAC AGA TCC AAC CAC
GAC ATC TCC AAC TTC GCT AAC TTG GCT TGG GAC GCT
AGA GAA AAG TTC GGT TGT GCT GTT GTT AAC TGT CCA
TTG GGT GAA ATC GAC GAC GAA ACT AAC CAC GAC GGT
GAA ACT TAC GCT ACT ACT ATC CAC GTT GTT TGT CAC
TAC CCA AAG ATC AAC AAG ACT GAA GGT CAA CCA ATC
```

-continued

```
TAC AAG GTT GGT ACT CCA TGT GAC GAC TGT TCC GAA
TAC ACT AAG AAG GCT GAC AAC ACT ACT TCC GCT GAC
CCA GTT TGT ATC CCA GAC GAC GGT GTT TGT TTC ATC
GGT TCC AAG GCT GAC TAC GAC TCC AAG GAG TTC TAC
```

-continued
AGA TTC AGA GAA TTG GGC GGT GGC GGT GGC

TTC CCA AGA CCA GGT AGC GGT GGC AAC GGT GAC TTC

GAA GAA ATC CCA GAA GAA TAC TTG

The TNHH gene is prepared by the following steps:
synthesizing 4 primers of P1, P2, P3 and P4, using the recombinant plasmid pUC57-NHH as a template, amplifying NIF gene (comprising a base sequence at the terminal region for encoding FPRP (SEQ ID No: 11)) with primers P1 and P2 and amplifying Hirulog gene (comprising a base sequence at the front region for encoding FPRP (SEQ ID No: 11)) with primers P3 and P4; then using NIF gene and Hirulog gene as the templates and amplifying TNHH gene with primers P3 and P4. Nde I and BamH I sites were added to the front and the terminal regions of the TNHH gene, respectively, for conveniently inserting TNHH gene into the prokaryotic expression vector pET-3c. The primer sequences were shown as the following (P1, P2, P3 and P4 were shown as SEQ ID NO: 4, 5, 6 and 7, respectively):

P1 (forward):
5'-CG CAT ATG AAC GAA CAC AAC TTG AGA TGT CCA-3'

P2 (reverse):
5'-ACC TGG TCT TGG GAA GCC ACC GCC ACC GCC CAA TTC TCT GAA-3'

P3 (forward):
5'-GGC TTC CCA AGA CCA GGT AGC GGT GGC AAC GGT GAC TTC-3'

P4 (reverse):
5'-TG GGA TCC TTA CAA GTA TTC TTC TGG GAT TTC-3'

CATATG: Nde I site; GGA TCC: BamH I site; the amino acid sequence encoded by the framed base pairs was FPRP (SEQ ID No: 11); and the amino acid sequence encoded by the boldfaced base pairs was GGGGG (SEQ ID No: 10) or GSGG (SEQ ID No: 12).

The reaction system used for amplifying target TNHH gene by overlap extension PCR was shown as the following: each PCR reaction system was set according to the manufacturer's instruction of PCR Reaction Kit (TaKaRa, Dalian) (Table 1).

NIF gene of 810 bp (shown in lane 2, FIG. 1) was amplified by use of recombinant plasmid pUC57-NHH as a template and P1 and P2 as primers. Hirugen gene of 70 bp (shown in lane 1, FIG. 1) was amplified by use of recombinant plasmid pUC57-NHH as a template and P3 and P4 as primers. TNHH gene of 870 bp (shown in lane 3, FIG. 1) was ultimately amplified by use of the gel-purified NIF gene and hirugen gene as templates and P1 and P4 as primers.

TABLE 1

| PCR reaction system | |
|---|---|
| Template | 1 μl |
| Upstream primer (25 pmol/L) | 2 μl |
| Downstream primer (25 pmol/L) | 2 μl |
| dNTPs (2.5 mmol/L for each base) | 8 μl |
| 10 × PCR buffer | 10 μl |
| MgCl₂ (25 mmol/L) | 10 μl |
| Taq DNA polymerase | 1 μl |
| ddH₂O | 66 μl |
| Total volume | 100 μl |

The reaction system was mixed thoroughly and centrifuged, and then 40 μl paraffin oil was added into the reaction system.

Reaction parameters used were as the following:

| 94 | pre-denaturation 3 min, | |
|---|---|---|
| 94 | 1 min | ⎫ |
| 55 | 1 min | ⎬ 35 cycles |
| 72 | 1.5 min | ⎭ |
| 72 | 10 min | |

After the reaction, 3 μl of reaction product was removed for the detection of the PCR result by 1.0% agarose gel electrophoresis (FIG. 1).

The PCR result showed that the target DNA fragments were amplified at each PCR step, and the TNHH gene was obtained. The sequence of the TNHH gene was identified by: enzymatically digesting TNHH gene and vector pLEX (Invitrogen) with Nde I and BamH I, recovering the target fragments, ligating with T4 DNA ligase to form recombinant plasmid pLEX-TNHH, and sequencing (TaKaRa, Dalian). The sequencing result demonstrated the complete identity between the amplified TNHH gene and the designed sequence.

Example 3

Construction of Recombinant Plasmid

1. Main Materials

Host bacteria E. coli BL21(DE3)pLysS, E. coli DH5α, plasmid pET3c (Novagen), DNA Extraction and Purification Kit (Shanghai Huashun Bioengineering Co., Ltd.), λDNA/Hind III+EcoRI Marker (Huamei), tool enzymes: Nde I, BamH I, Hind III, DNA Ladder Marker, DNA Recovery Kit and DNA Ligation Kit Ver. 2.1 (TaKaRa, Dalian), antibiotics Ampicillin, Streptomycin, Tetracycline, Kanamycin (AMRESCO).

2. Methods

The pLEX-TNHH was enzymatically digested by Nde I and BamH I and the target fragments were obtained. DNA Ligation Kit was used for ligating TNHH gene with the large fragment of plasmid pET3c obtained by enzymatic digestion with Nde I and BamH I. Competent E. coli DH5α was prepared according to CaCl₂ method and transformed. The transformed E. coli DH5α was spread on LB plate comprising 100 mg/L ampicillin. The LB plate was incubated in an incubator at 37 for 12 h to obtain opalescent translucent single colony. The single colony was picked up with sterile toothpicks and cultured in LB liquid medium comprising 100 mg/L ampicillin for the plasmid extraction. The expression plasmid pET3-TNHH comprising a chimeric fragment of 860 bps was screened by enzymatic digestion with Nde I and BamH I.

Plasmid Extraction

The extraction procedures were performed according to the manufacturer's instruction of DNA Extraction and Purification Kit.

Enzymatic Digestion

Figure 2:
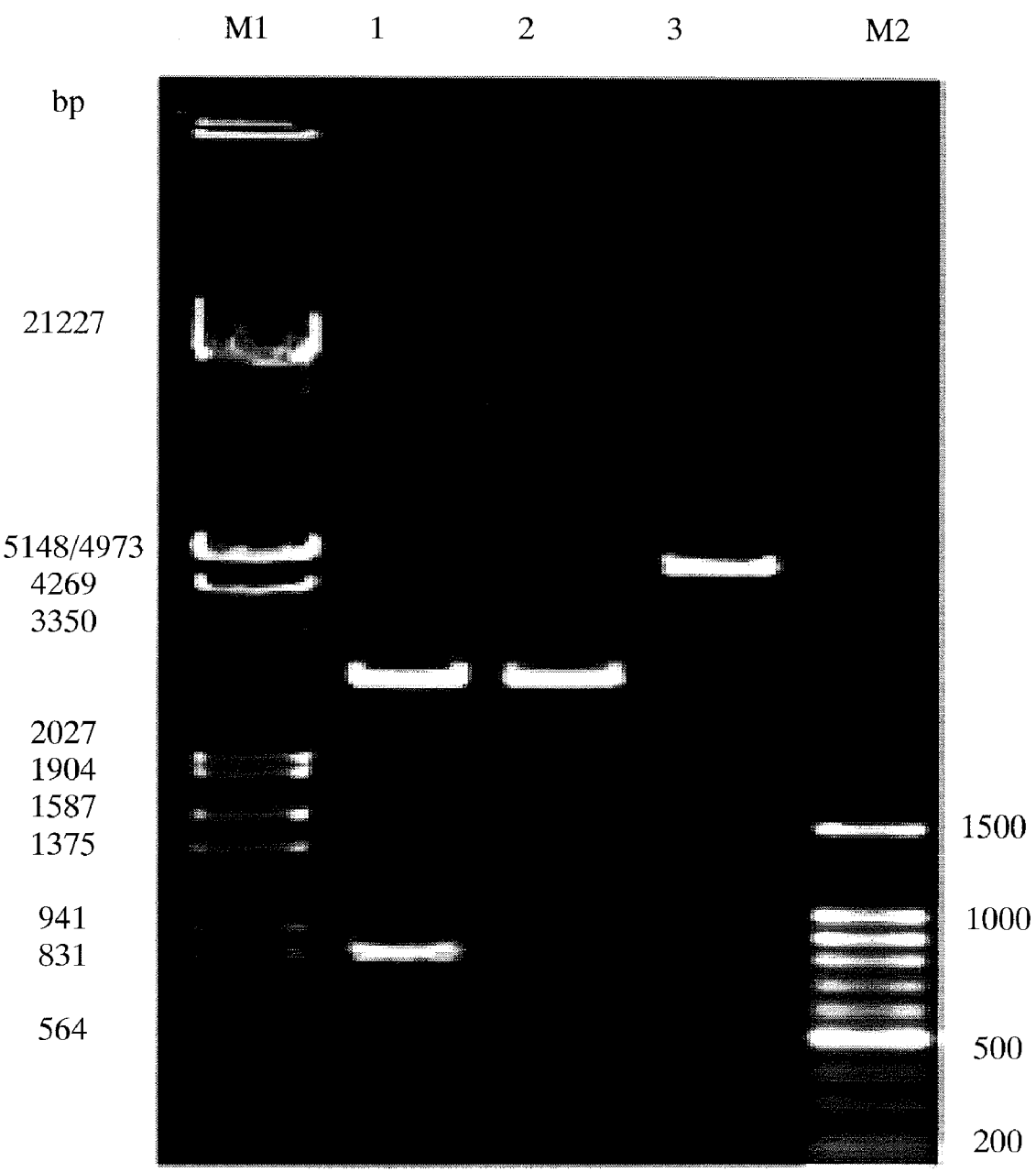

The plasmid pLEX-TNHH and plasmid pET3c were digested respectively. The reaction system was plasmid DNA 0.5 μg, BamH I 1.0 U, NdeI 1.0 U, 10× enzyme reaction buffer solution 2.0 μl, and adding deionized water (DDW) to 20 μl. Enzymatic digestion was performed in the incubator at 37 for 2 h. 1 μl digested plasmid was taken from each reaction and detected by 1% agarose gel electrophoresis. The digested pLEX-TNHH showed a band of 860 bps and a band of 2900 bps, and the digested pET3c showed a band of 4600 bps (FIG. 2).

Ligation of pET-3c and TNHH Gene

Figure 3:
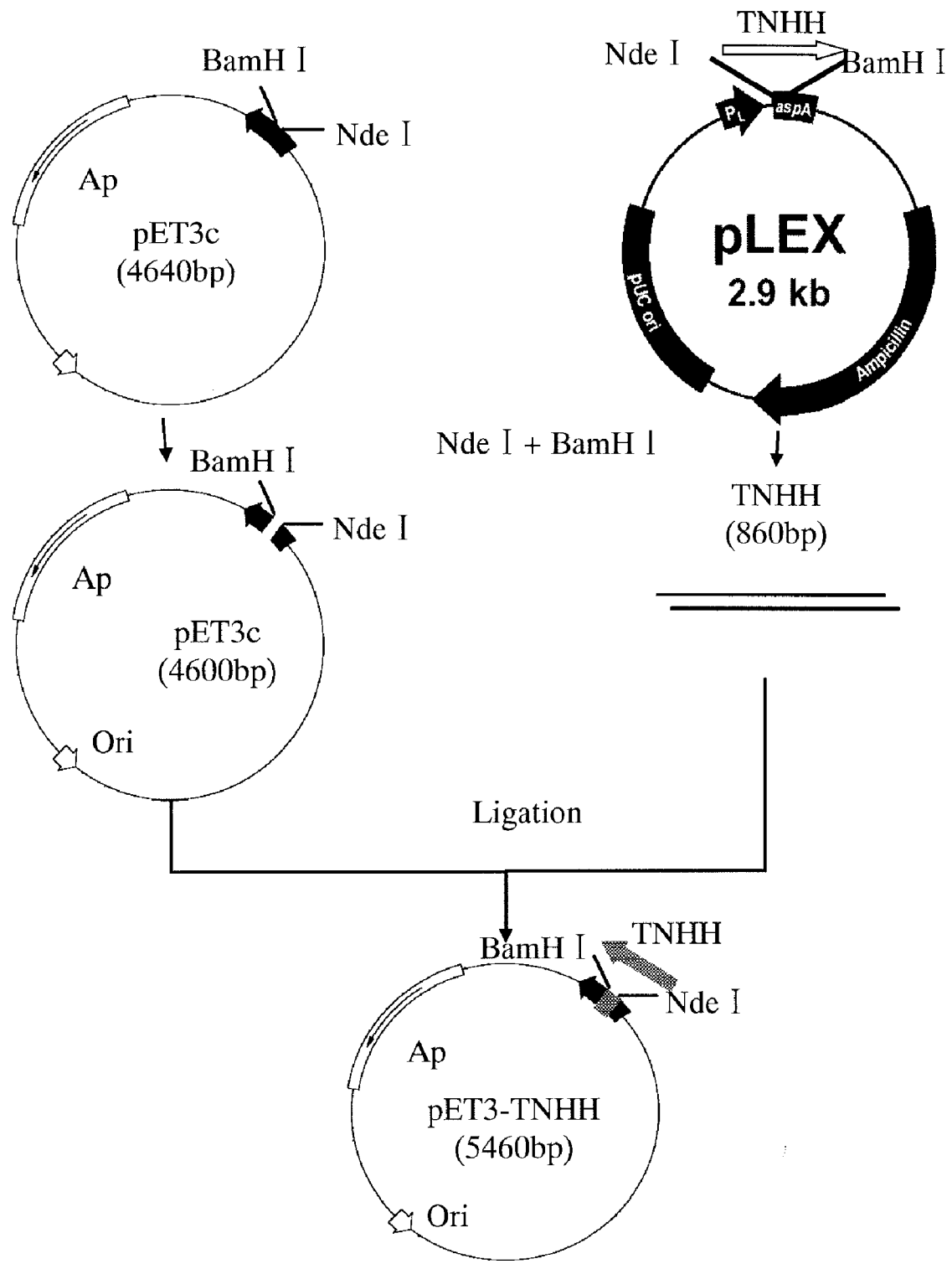

All digested samples were recovered by gel electrophoresis, and the target fragment from the digested pLEX-TNHH plasmid and the linearized pET-3c were recovered according to the manufacturer's instruction of DNA Recovery Kit. The recovered linearized pET-3c and the target fragment were ligated at 16 for 30 min according to the manufacturer's instruction of DNA Ligation Kit to obtain the pET3-TNHH (FIG. 3).

Preparation and Transformation of Competent Cells

Preparation of competent *E. coli* DH5α and *E. coli* BL21 (DE3)pLysS and the transformation of pET3-TNHH are performed according to the conventional calcium chloride method (Molecular Cloning, Second edition, P55).

Example 4

1. Ligation and Transformation

*E. coli* DH5α was transformed by the pET3-TNHH positive ligation solution and the pET3-TNHH negative ligation solution, respectively. *E. coli* DH5α was separately spread on two LB plates comprising 100 mg/L ampicillin for each and incubated at constant temperature of 37 for 12 h. 5 single colonies were observed on the negative plate, and about 100 single colonies were observed on the positive plate, demonstrating the successful ligation and transformation. The colonies showed typical morphology of *E. coli*.

Figure 4:
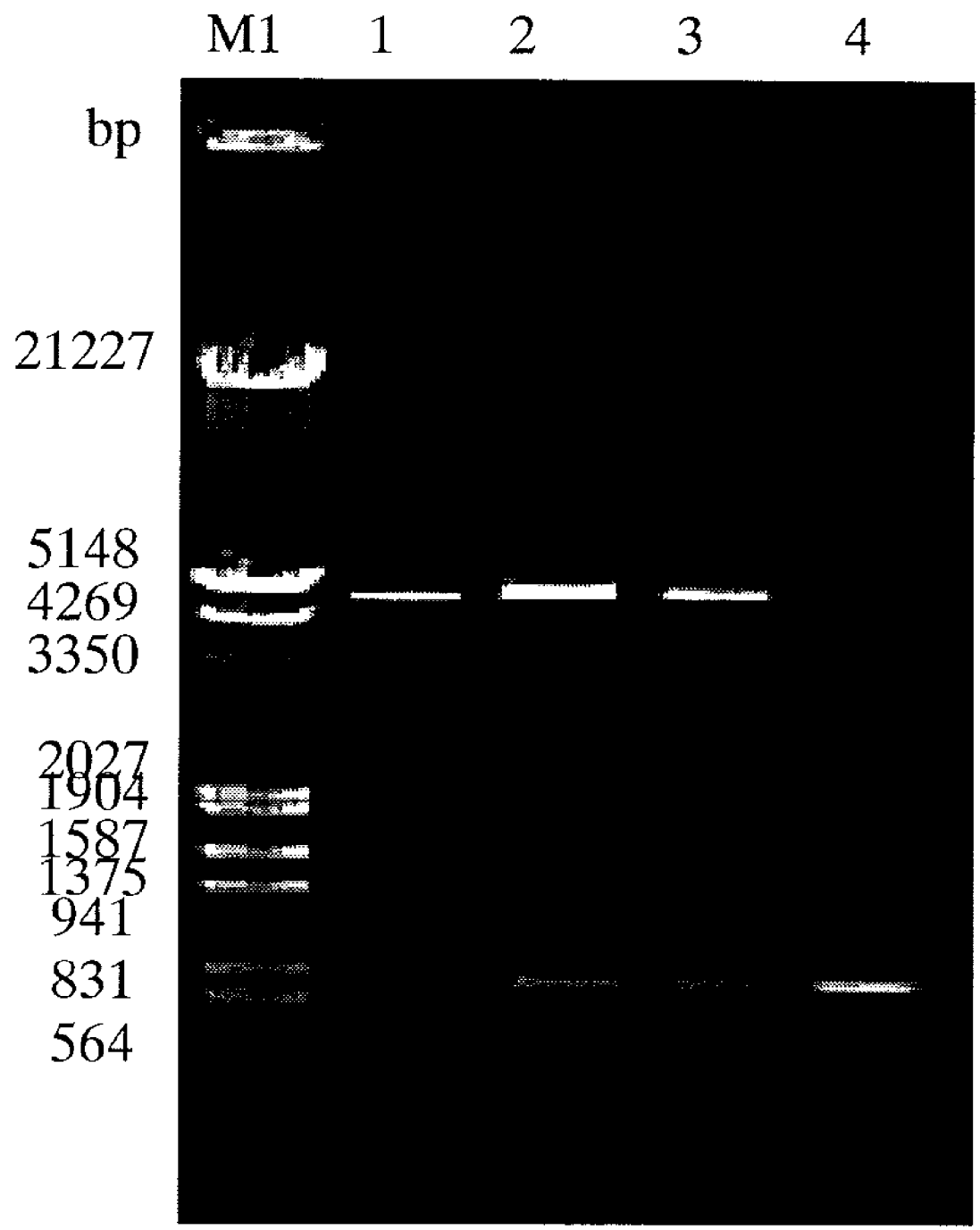

2. Identification of Recombinant Expression Plasmid pET3-TNHH by Enzymatic Digestion Two single colonies were picked up with sterile toothpicks from the positive plate and then cultured in the LB liquid medium comprising 100 mg/L ampicillin at 37 for 12 h. Subsequently, the recombinant expression plasmid pET3-TNHH was extracted and digested with Nde I and BamH I. The results showed a band of 4600 bp and a band of 860 bp (using the PCR product of TNHH as a control) as expected (FIG. 4).

3. Identification of Recombinant Expression Plasmid pET3-TNHH by Sequencing

Extracting plasmid pET3-TNHH from pET3-TNHH/*E. coli* DH5α, and performing sequence analysis after identification by enzymatic digestion. The sequencing results (obtained by TaKaRa, Dalian) showed the TNHH sequence contained in the plasmid was the same as expected.

Example 5

Extraction and Purification of TNHH

The pET3-TNHH/BL21(DE3)pLysS engineering bacteria were inoculated into the LB medium (comprising 100 µg/ml Amp), and cultured at 30 and 250 rpm for 1.5-3 hr. When OD value reached 0.4-0.6, 0.5 mM IPTG (final concentration) was added for 3-4 hr induction. The engineering bacteria were collected and lysed, and TNHH was extracted and purified.

Detailed procedures were as shown as the following:

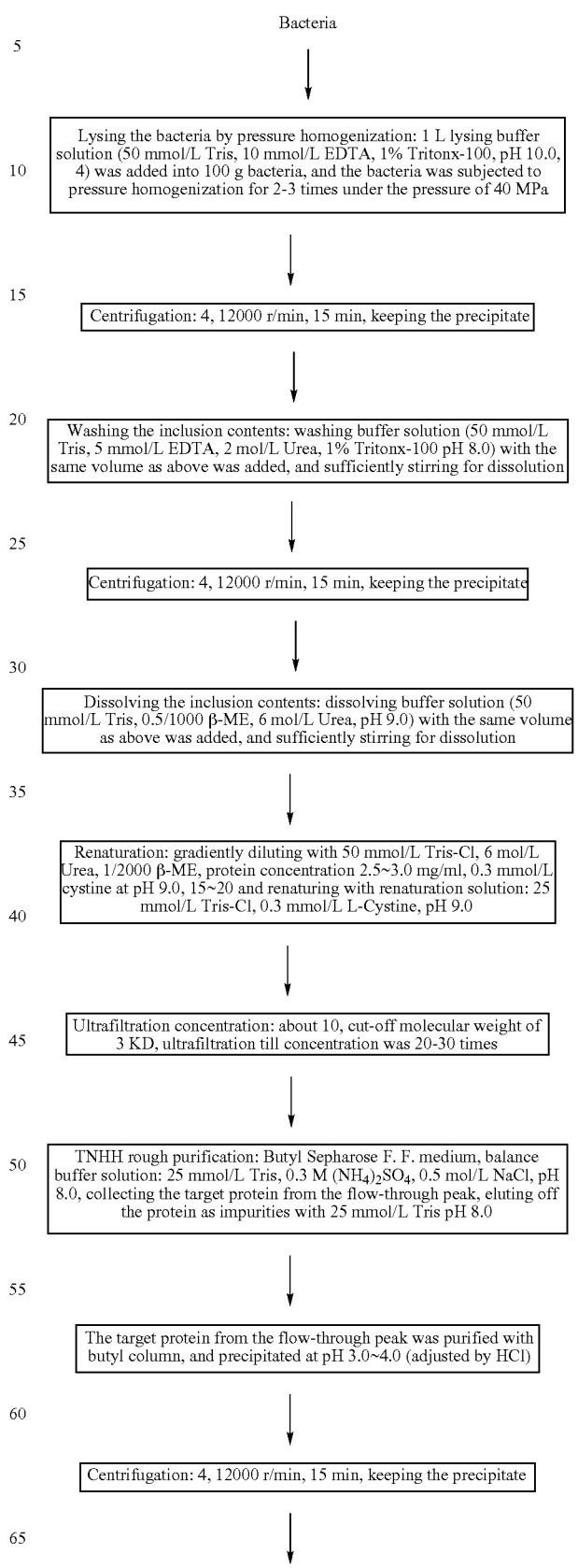

-continued

```
Dissolving the precipitate in 20 mmol/L PB pH 8.0 buffer solution to
obtain a clear solution and filtering with 0.45 μm membrane
                            ↓
TNHH fine purification: Source 30 Q, medium, balance buffer A:
20 mmol/L PB, 0.2 mol/L NaCl, pH 8.0, eluting condition B (20 mmol/L
PB 0.5 mol/L NaCl pH 8.0), linear gradient eluting, collecting interest
              protein peak (about 35% B solution)
                            ↓
   Interest protein was purified with Source 30 Q column, and
    precipitated at pH 3.0~4.0 (adjusted by phosphoric acid)
                            ↓
    Centrifugation: 4, 12000 r/min, 15 min, keeping the precipitate
                            ↓
   Completely dissolving the precipitate with 10 mmol/L PB, pH 7.4
         buffer solution and filtering with 0.45 μm film
                            ↓
   Removing heat source and some high molecular weight protein:
   Superdex 75 medium, balance buffer: 10 mmol/L PB pH 6.5, eluting
         condition for interest protein: 10 mmol/L PB pH 6.5
                            ↓
                    Mother liquid of TNHH
```

The mother liquid of TNHH thus obtained was diluted with 10 mmol/L PB (pH7.5) till the concentration of TNHH reached 3.0 mg/ml, and then freeze-dried to obtain the product after the addition of mannitol 4.0%.

Example 6

Identification of the Mother Liquid of TNHH by Immunoblotting and Sequencing

The purified TNHH was analyzed by SDS-PAGE gel electrophoresis with the same sample-loading amount, and then transferred onto nitrocellulose film with an electro-transferring apparatus for binding first with mouse anti-hirudin antibody (primary antibody) and then binding with goat-anti-mouse IgG-HRP (secondary antibody). The immunoblotting results were obtained by color-developing reactions with substrates (FIG. 5).

Figure 5:
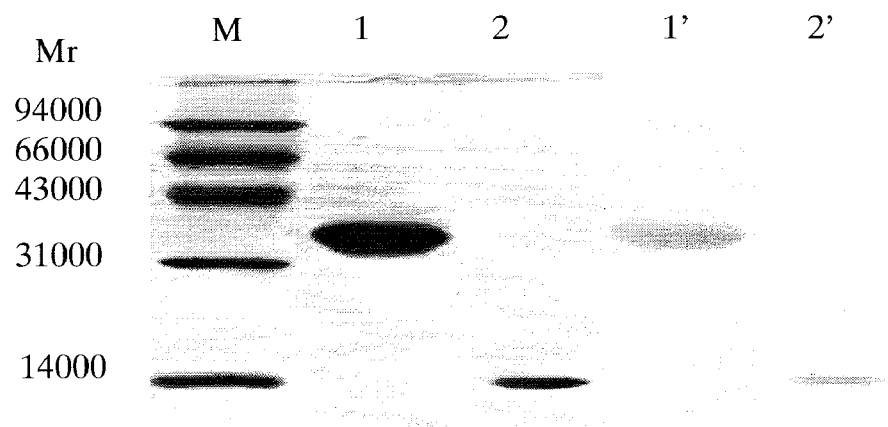
Figure 6:
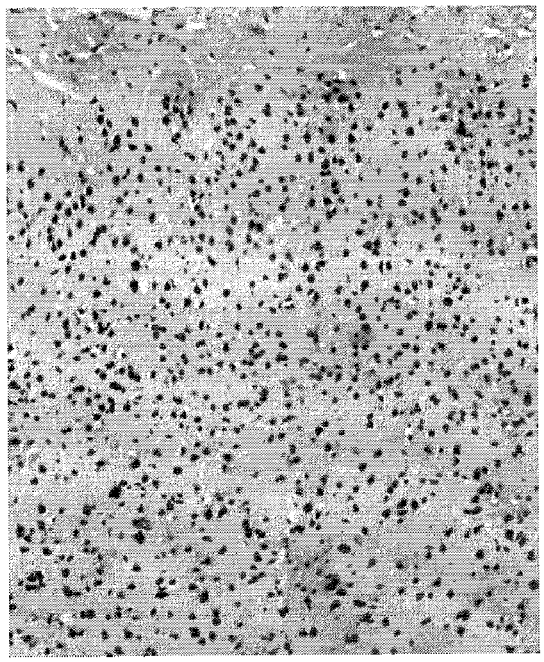
Figure 7:
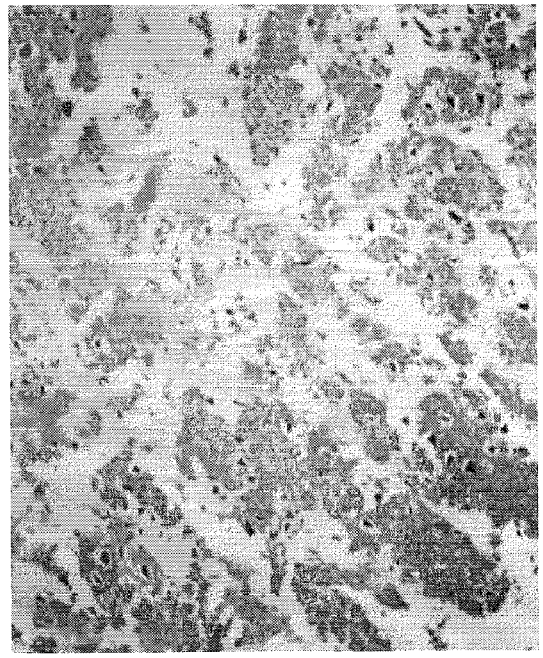
Figure 8:
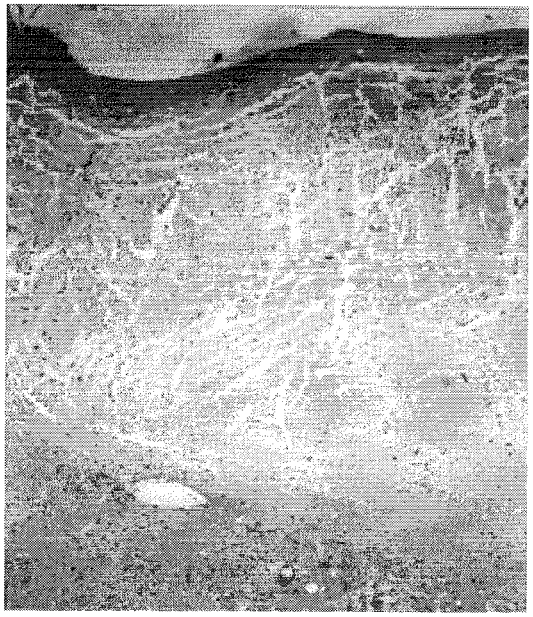
Figure 9:
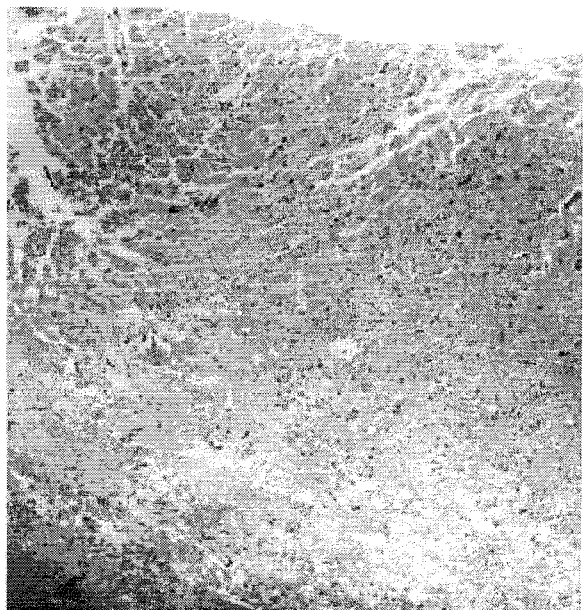

It can be seen from FIG. 5 that there was the component specifically binding the anti-hirudin antibody within the TNHH, suggesting that the designed HV2 antigen epitope was adequately exposed and could specifically bind with the antibody.

The sequencing results showed that N-terminal amino acid sequence of the TNHH was MNEHNLRCPQNGTEM (SEQ ID No: 16), and the C terminal amino acid sequence of the TNHH was EYL, both of which are consistent with those of the designed sequence:

```
                                      (SEQ ID NO: 3)
MNEHNLRCPQNGTEMPGFNDSIRLQFLAMHNGYRSKLALGHISITEESES

DDDDDFGFLPDFAPRASKMRYLEYDCEAEKSAYMSARNCSDSSSPPEGYD

ENKYIFENSNNISEAALKAMISWAKEAFNLNKTKEGEGVLYRSNHDISNF

ANLAWDAREKFGCAVVNCPLGEIDDETNHDGETYATTIHVVCHYPKINKT

EGQPIYKVGTPCDDCSEYTKKADNTTSADPVCIPDDGVCFIGSKADYDSK

EFYRFRELGGGGGFPRPGSGGNGDFEEIPEEYL.
```

The identity between the amino acid sequence of TNHH and the designed sequence was further determined in light of the DNA sequencing results.

Amino acid sequence in the front of the (Gly)$_5$ (SEQ ID No: 10) was NIF, and the amino acid sequence of hirudin was NGDFEEIPEEYL (SEQ ID No: 17).

It can be seen from above results that the obtained TNHH had a structure of Met-NIF-GGGGG-FPRPGSGG (SEQ ID No: 15)-Hirugen.

Example 7

Preparation of TNHH Comprising Linker 1 (Gly)$_{15}$ (SEQ ID No: 18) and Linker 2 (GSGG)$_3$ (SEQ ID No: 14)

The linker 1 and the linker 2 within the TNHH gene were replaced by PCR to obtain NIF-(Gly)$_{15}$-FPRP-(GSGG)$_3$ (SEQ ID No: 19)-hirugen.

Two pairs of primers were synthesized:

P5 (forward): the same as P1 in Example 2

```
P6 (reverse):
                                       (SEQ ID No: 8)
5'-ACC TGG TCT TGG GAA GCC ACC GCC ACC GCC ACC

GCC ACC GCC ACC GCC ACC GCC ACC GCC CAA TTC TCT

GAA-3'

P7 (forward):
                                       (SEQ ID No: 9)
5'-GGC TTC CCA AGA CCA-GGT AGC-GGT GGC GGT AGC

GGT GGC GGTAGC GGT GGC AAC GGT GAC TTC-3'
```

P8 (reverse): the same as P4 in the example 2, wherein the amino acid sequence encoded by the framed base pairs was FPRP (SEQ ID No: 11); the amino acid sequence encoded by the boldfaced base pairs in P6 was (Gly)$_{15}$ (SEQ ID No: 18); and the amino acid sequence encoded by the boldfaced base pairs in P7 was (GSGG)$_3$ (SEQ ID No: 14).

The interest gene was prepared by use of TNHH polynucleotide as the template, and performing PCR according to the method used in examples 2, 3, 4, and 5. Then constructing the recombinant plasmid, ligating, transforming, identifying, extracting and purifying are performed.

The obtained recombinant TNHH was designated as TNHH-G$_{15}$/n$_3$.

In vitro comparative analysis, it is demonstrated that TNHH-G$_{15}$/n$_3$ and TNHH have the same antithrombin activity and anti-leukocyte adhesion activity.

Two pairs of primers were synthesized:

P5 (forward): the same as P1 in the example 2

P6 (reverse):
(SEQ ID No: 8)
5'-ACC TGG TCT TGG GAA GCC ACC GCC ACC GCC ACC GCC ACC GCC ACC GCC ACC GCC ACC GCC CAA TTC TCT GAA-3'

P7 (forward):
(SEQ ID No: 9)
5'-GGC TTC CCA AGA CCA-GGT AGC-GGT GGC GGT AGC GGT GGC GGT AGC GGT GGC AAC GGT GAC TTC-3'

P8 (reverse): the same as P4 in the example 2, wherein the amino acid sequence encoded by the framed base pairs was FPRP (SEQ ID No: 11); the amino acid sequence encoded by the boldfaced base pairs in P6 was $(Gly)_{15}$ (SEQ ID No: 18); and the amino acid sequence encoded by the boldfaced base pairs in P7 was $(GSGG)_3$ (SEQ ID No: 14).

|  | antithrombin activity (ATU/mg) | anti-leukocyte adhesion activity (Unit/mg) |
|---|---|---|
| TNHH | 1200 | 750 |
| TNHH-$G_{15}$/$n_3$ | 1200 | 740 |
| NHH | 800 | 650 |
| NIF | None | 750 |
| Hirogen | 1000 | none |

Example 8

A Pharmaceutical Composition Comprising TNHH 8.1 Injections

The mother liquid of the recombinant TNHH protein from Example 5 was formulated according to the following formulation to prepare an injection, wherein the concentration of TNHH was a final concentration.

| Formulation A: | |
|---|---|
| TNHH | 3.0 mg/ml |
| $Na_2HPO_4$/$NaH_2PO_4$ | 10 mmol/L |
| PH | 7.0-8.0 |

| Formulation B: | |
|---|---|
| TNHH | 6.0 mg/ml |
| sodium acetate/acetic acid | 20 mmol/L |
| Glycerol | 20 mg |
| PH | 5.5-7.0 |

8.2 Lyophilized Powder

The mother liquid of the recombinant TNHH protein from the example 5 was formulated according to the following formulation to prepare the lyophilized powder, wherein the concentration of TNHH was a final concentration.

| Formulation C: | |
|---|---|
| TNHH | 3.0 mg |
| $Na_2HPO_4$/$NaH_2PO_4$ | 10 mmol/L |
| glycine | 40 mg |
| PH | 6.0-8.0 |

| Formulation D: | |
|---|---|
| TNHH | 6.0 mg |
| sodium acetate/acetic acid | 10 mmol/L |
| sucrose | 60 mg |
| PH | 5.0-6.0 |

| Formulation E: | |
|---|---|
| TNHH | 9.0 mg |
| sodium bicarbonate/sodium carbonate | 20 mmol/L |
| trehalose | 40 mg |
| PH | 8.0-9.0 |

The preparation processes in Example 8 were all followed the conventional processes for the preparation of injections and lyophilized powders.

The following examples were experiments on TNHH of present invention for determining the biological activities thereof. All TNHH samples in the experiments were the TNHH products from the example 5; NIF and NHH were prepared by Chongqing Fujin Biology and Medicine Company according to Chinese Patent Application No. 031011551.

Example 9

Comparison of the Therapeutic Effects of NIF, NHH and TNHH on Cerebral Ischemic Injury in Rats Subjected to Middle Cerebral Artery Occlusion 1. Materials Medicaments: Test medicaments were NIF, NHH and TNHH.

Agents: Triphenyltetrazolium chloride (TTC), purchased from China National Medicine Group, Shanghai Chemical Reagent Company, Lot No.: F20020610; APTT kit, purchased from Shanghai Sunbiote Company, Lot No.: Medical Device Registration Record JIN (2002) No. 3401632.

Animals: 24 Wistar rats, male, 18~230 g, provided by Animal Center, Chongqing Medical University.

2. Methods

Wistar rats were randomly divided into 4 groups (6 animals per group), including model group, NHH group, NIF group and TNHH group. Then anaesthesia was performed to each Wistar rat using 10% chloral hydrate (350 mg/kg, i.p.). The rat was fixed in supine position and the skin was dissected along the median incision of neck to seek out the right common carotid artery which was then threaded with 2 sutures for later application. The external carotid artery was subsequently separated and ligated. The internal carotid artery and pterygopalatine artery under the external carotid artery were isolated and the later one was ligated as well. The proximal end and distal end of the common carotid artery isolated were clipped, and then a small incision was opened on the external carotid artery, in which a nylon thread ($\Phi$=0.22~0.30 mm) was inserted. Then the thread was pushed to the anterior cerebral artery (about 20 mm) slowly and pulled back about 2 mm to arrive at the orifice of middle cerebral artery (about 17 mm in length). Subsequently, the artery clips were removed after fixation of the nylon thread by ligation with No. 7 suture, and then the muscle and skin were sutured. After surgery, the rat was raised alone in a large cage. After got conscious, the rats was evaluated based on the behavior score, by which successful establishment of animal model was indicated when it was scored <11. Corresponding drugs (2 mg/kg, bid) were administered through the caudal vein to animals with administration volume of 1 ml/100 g in each group after model animal was successfully established (according to the score less than 11 based on the behavior score evaluation), while the model group received physiological saline in the corresponding volume. Neuroethological score (with full score of 11) was evaluated at the 4 h, 12 h, 24 h, 48 h and 72 h after surgery. After evaluated at the 72 h, 1.8 ml blood was sampled by carotid artery catheter and rapidly added to a silicified tube which contained 0.2 ml of 0.109 mol/L anticoagulant sodium citrate. After mixed thoroughly by slightly shaking, it was then centrifuged at 300 rpm for 15 min. The supernatant was collected to determine APTT according to the reagent instruction. Subsequently, the rats were sacrificed by decapitation, and the cranium was removed to expose the brain. After removal of olfactory bulb, cerebellum and lower brainstem, the remaining part was weighed, and then the cerebrum was sliced into five pieces along the coronal section. The brain slices were placed into phosphate buffer comprising 4% TTC and incubated at 37 for 30 min. The slices were turned over for 3-4 times during incubation. The normal brain tissue was stained to be red, while the infarcted brain tissue was white. Then the white infarction area was cut and weighed. The proportion of infarcted brain tissue in the total brain weight was calculated as infarction area using "weigh-area method".

Another two animals in each group were selected for pathological examination of brain after sacrifice.

3. Results 3.1 Comparison of the Behavioral Scoring of NIF, NHH and TNHH on Cerebral Ischemia in Rats Subjected to Middle Cerebral Artery Occlusion As indicated in the table 2, NIF, NHH and TNHH could obviously improve the behavioral scoring of the cerebral ischemia in rats subjected to middle cerebral artery occlusion, and there were difference and significant difference between the treatment group and the model group (P<0.05 and P<0.01).

TABLE 2

Comparison of the behavioral scoring of NIF, NHH and TNHH on cerebral ischemia in rats subjected to middle cerebral artery occlusion

| Groups | Animals | Behavioral score | | | | |
|---|---|---|---|---|---|---|
| | | 4 h | 8 h | 24 h | 48 h | 72 h |
| Model group | 6 | 8.5 ± 1.6 | 8.2 ± 1.5 | 8.0 ± 1.7 | 8.0 ± 2.0 | 8.0 ± 2.0 |
| NIF group | 6 | 6.2 ± 0.8* | 6.5 ± 1.2 | 5.5 ± 0.5** | 5.5 ± 0.4* | 5.5 ± 0.5* |
| NHH group | 6 | 8.2 ± 1.7 | 8.2 ± 1.7 | 8.0 ± 1.4 | 6.5 ± 1.4* | 5.7 ± 1.2* |
| TNHH group | 6 | 6.5 ± 1.0 | 6.2 ± 1.2* | 5.8 ± 1.2* | 5.3 ± 0.5** | 5.0 ± 0.6** |

Compared with the model group, *P < 0.05, **P < 0.01, the same for hereinafter.

3.2 Comparison of the Effects of NIF, NHH and TNHH on Cerebral Infarction Volume in Rats Subjected to Middle Cerebral Artery Occlusion As shown in the table 3, NIF, NHH and TNHH could obviously decrease the cerebral infarction volume in rats subjected to middle cerebral artery occlusion, and there were difference and significant difference between the treatment group and the model group (P<0.05 and P<0.01).

TABLE 3

Comparison of the effects of NIF, NHH and TNHH on cerebral infarction volume in rats subjected to middle cerebral artery occlusion

| Groups | Animals | Cerebral infarction volume (%) |
|---|---|---|
| Model group | 4 | 39.4 ± 5.7 |
| NIF group | 4 | 24.9 ± 9.6* |
| NHH group | 4 | 25.2 ± 5.2** |
| TNHH group | 4 | 23.2 ± 5.4** |

3.3 Results of Pathological Section for the Effects of NIF, NHH and TNHH on Cerebral Infarction Volume in Rats Subjected to Middle Cerebral Artery Occlusion Compared with the brain tissues in the normal control group, in the model group and the treatment group, the nerve cells in the cerebral cortex had an irregular structure at different levels, deeply stained and pyknotic nucleus, and shrunk cell bodies. Pyramidal cells in hippocampus CA1 area had an irregular structure at different levels, loose cell arrangement, lightly stained cytoplasm, deeply stained and pyknotic nucleus, and decreased numbers of cell bodies to different extents. Compared with the model group, NIF group, NHH group and TNHH group had less pathological changes. TNHH group had the least pathological changes (FIGS. 6-11).

The above pathological section results showed that NIF, NHH and TNHH groups, compared with the model group, had protective effects on cerebral infarction in rats subjected to middle cerebral artery occlusion, wherein the cerebral ischemic necrosis in the TNHH group was the least.

4. Conclusions

There were obviously therapeutic effects of NIF, NHH and TNHH on cerebral ischemic injury in rats subjected to middle cerebral artery occlusion, and the TNHH had the most obviously therapeutic effects.

Example 10

Comparison of the Effects of NIF, NHH and TNHH on Experimental Cerebral Hematoma in Rats 1. Materials Medicaments: Test medicaments NIF, NHH and TNHH, provided by Chongqing Fujin Biology and Medicine Company Animals: 32 SD rats, male, 18~230 g, provided by Animal Center, Daping Hospital, Third Military Medical University.

2. Methods 2.1 Establishment of Cerebral Hemorrhage Model in Rats

SD rats were randomly divided into 4 groups (8 animals per group), including model group, NHH group, NIF group and TNHH group. The rats in each group were anesthetized by chloral hydrate, and then 0.1 ml blood was collected by amputation of tail. The rats were fixed in a stereotaxic apparatus. Median incision of scalp was performed and the periosteum was cut open to expose bregma. Subsequently, a small hole with a diameter of 1 mm was perforated for needle insertion of microsyringe fixed on the stereotaxic apparatus with insertion depth of 5.8 mm (i.e to the position of caudate nucleus) at the site which was 1 mm rearward to the bregma and 3 mm left to the midline, and then 0.1 ml autoblood was injected slowly. Neurological functional defect score was immediately evaluated based on the evaluation criterion after the animal got conscious. The animal with behavior score less than 11 was selected in this study. Behavior score evaluation was continuously carried out after the establishment of model till the end of the experiment.

2.2 Observation Index

The neurologic function defect score was evaluated at 5 time points of 4 h, 12 h, 24 h, 48 h and 72 h after the model establishment. Changes of brain water content and histopathological observation were performed at 72 h after the model establishment on sacrificed rats.

2.3 Administration Methods

Corresponding medicaments (2 mg/kg, bid) were administered through the caudal vein to animals with administration volume of 1 ml/100 g in each group after model animal was successfully established (according to the score less than 11 based on the behavior score evaluation), while the model group received physiological saline in the corresponding volume.

2.4 Determination of Brain Water Content

The brain was taken out immediately after the sacrifice of animals, and then 150-200 g ectocinerea (cortex was removed) at the edge of haematoma was collected. The brain water content was determined using dry and wet method based on the following formula:

Brain water content=(wet weight−dry weight)/wet weight×100%

2.5 Observation by Ordinary Light Microscope

The brain was immediately taken out by decollation at selected time points, and it was sliced up to be 2 mm thick along the coronal section and then fixed in 10% formaldehyde. The slices were stained by regular HE and mounted. Then the pathological changes occurred in pathological region and the neighboring brain tissues were observed.

2.6 Evaluation of Behavior Index

Evaluation was performed at the time of 4 h, 12 h, 24 h, 48 h and 72 h after surgery. The method was described as follows:

The flection of forelimbs was observed by lifting the rat by its tail. If the forelimbs symmetrically extended toward the floor, the score was 0. While if wrist flection, or elbow inflection, or internal rotation of shoulder, or both elbow inflection and internal rotation of shoulder occurred to forelimbs of the rat on the opposite side of the surgery part, it was evaluated as scores of 1, 2, 3 and 4, respectively.

The animal was placed on flat floor, and then both shoulders were pushed to move towards the opposite side to examine the resistance. If the resistances on both sides were equal and forceful, it was evaluated as 0. While if the resistance decreased slightly, mildly or severely when pushed to the opposite side of the surgery part, it was evaluated as 1, 2 or 3, respectively.

Both forelimbs of the animal were placed on a metal mesh to observe the muscular tension. The rat with equal and forceful muscular tension of both forelimbs was evaluated as 0. In the same way, the rat was evaluated as 1, 2 or 3, respectively with the reduction of muscular tension on the opposite side of the surgery part mentioned above.

The animal tended to keep turning around to one side was evaluated as 1. Based on the evaluation criterion (with full score of 11), the higher the score was evaluated, the more severe the behavior disorder was.

3. Results 3.1 Comparison of the Effects of NIF, NHH and TNHH on Behavior Score of Rats with Experimental Cerebral Hematoma It could be seen from table 5 that the behavior score of rats with experimental cerebral hematoma was significantly improved by NIF, NHH and TNHH, and the results in various treatment groups were significantly or very significantly different from that in the model group ($P<0.05$ and $P<0.01$).

TABLE 5

Comparison of the effects of NIF, NHH and TNHH on behavioral scoring in rats subjected to experimental cerebral hematoma

| Groups | Animals | behavioral score | | | | |
|---|---|---|---|---|---|---|
| | | 4 h | 12 h | 24 h | 48 h | 72 h |
| Model group | 8 | 2.50 ± 0.84 | 2.83 ± 0.75 | 3.83 ± 1.72 | 5.33 ± 1.63 | 6.17 ± 1.47 |
| NIF group | 8 | 1.86 ± 0.90 | 2.14 ± 0.90* | 2.43 ± 0.53** | 3.14 ± 0.90** | 4.14 ± 1.68** |
| NHH group | 8 | 2.14 ± 0.69 | 1.86 ± 0.90** | 2.43 ± 1.00** | 2.57 ± 0.13** | 3.57 ± 1.72** |
| TNHH group | 8 | 2.00 ± 1.07 | 2.00 ± 0.76** | 2.25 ± 0.46** | 2.12 ± 0.64** | 2.88 ± 1.46** |

Compared with the model group, *$P < 0.05$, **$P < 0.01$, the same for hereinafter.

3.2 Comparison of the Effects of NIF, NHH and TNHH on Brain Water Content in Rats Subjected to Experimental Cerebral Hematoma As shown in the table 6, NIF, NHH and TNHH could obviously decrease the brain water content in rats subjected to experimental cerebral hematoma, and there were difference and significant difference between the treatment groups and the model group ($P<0.05$ and $P<0.01$).

TABLE 6

Comparison of the effects of NIF, NHH and TNHH on behavioral score in rats subjected to experimental cerebral hematoma

| Groups | Animals | Brain water content (%) |
|---|---|---|
| Model group | 8 | 83.35 ± 2.07 |
| NIF group | 8 | 79.36 ± 0.47** |
| NHH group | 8 | 78.66 ± 0.55** |
| TNHH group | 8 | 78.28 ± 1.97** |

3.3 Observation Results of the Effects of NIF, NHH and TNHH on Pathological Section of Rats with Experimental Cerebral Hematoma Observation index: brain edema, nerve cell degeneration or necrosis, demyelination of never fiber, hyperplasia of glial cells, inflammatory cell infiltration and interstitial hemorrhage.

Observation on the contralateral brain in control group: the structure of cortex and encephala were clear, and the nerve cell, the glial cell, the distribution of vessels, and the structure of vessels were all normal, and no hydrocephalus, inflammatory cell infiltration or hemorrhage occurred.

In model group: the structure of cortex and encephala was unclear, and some nerve cells got denaturalized or necrotic, and significant brain edema and inflammatory cell infiltration occurred, and interstitial hemorrhage and hyperplasia of glial cell occurred. The degree of pathological change mentioned above was that most animals belonged to ++→+++ pathological change, while 2 cases belonged to + pathological change.

NIF group: most cases mentioned above belonged to ±→+ pathological change, while 3 cases belonged to +→++ pathological change.

NHH group: most cases mentioned above belonged to 0→+ pathological change, while 3 cases belonged to +→++ pathological change.

TNHH group: significant improvements of pathlogical change mentioned above were developed, and most cases belonged to 0→± pathological change, while only 2 cases belonged to ± pathological change.

4. Conclusions

NIF, NHH and TNHH showed obviously therapeutic effects on rats subjected to experimental cerebral hematoma, and the TNHH had the most obviously therapeutic effects.

Example 11

In Vitro Binding of TNHH to Fibrin and Thrombin

1. Test Materials
1.1 Medicaments

Mother liquid of TNHH (3.0 mg/ml); Human fibrin (1 g/ampoule, F5386), Sigma company. Human thrombin (127 Unit/ampoule), Lot No.: 20021105, National Institute for The Control of Pharmaceutical and Biological Products 1.2 Solutions Phosphate buffer solution (10 mmol/L PB, 0.15 mol/L NaCl, pH 7.4); Chromatography flow phase buffer solution: 20 mmol/L NaH2PO4-Na2HPO4, 0.15 mol/L $(NH_4)_2SO_4$, pH 6.8.

1.3 Instruments

Thermostatic water bath; Gel chromatographic column (Shodex PROTEIN KW-82.5). Waters 600 HPLC system, Zhejiang University N2000 chromatography workstation. One 1 ml EP support, plural 1 ml EP tubes, 1 ml pipettor and pipette tips.

2. Test Methods and Results
2.1 Test Materials

Weigh TNHH, dilute to 1.0 mg/ml with phosphate buffer solution, and is ready for use; Weight fibrin precisely, dissolve and dilute to 0.1 mg/ml with phosphate buffer solution, and is ready for use; Weigh thrombin, dissolve and dilute to 100 units/ml with phosphate buffer solution, which is ready for use.

2.2 Reaction of the Test Materials

Following the below procedures, test materials were reacted at 37° C. for 1 h, and then analyzed under the following chromatographic conditions.

(1) pipette test material solutions (20 μl for each), loading for analysis, and recording each retention time.

(2) pipette fibrin and thrombin solutions (0.5 ml for each), mixing and reacting at 37° C. for 1 h, and loading 20 μl sample for analysis.

(3) pipette TNHH and fibrin solutions (0.5 ml for each), mixing and reacting at 37° C. for 1 h, and loading 20 μl sample for analysis.

(4) pipette TNHH and thrombin solutions (0.5 ml for each), mixing and reacting at 37° C. for 1 h, and loading 20 μl sample for analysis.

(5) pipette TNHH and mixture of fibrin and thrombin solutions (0.5 ml for each), mixing and reacting at 37° C. for 1 h, and loading 20 μl sample for analysis.

2.3 Chromatographic Conditions

Flow rate 0.5 ml/min; detection wavelength: 214 nm, Column temperature: room temperature; chromatogram recording time: 25 min.

2.4 Chromatographic Results

TABLE 7

SEC-HPLC chromatographic results of binding TNHH to fibrin and thrombin

| Samples | retention time (min) peak 1 | peak 2 |
|---|---|---|
| TNHH (T) | 23.657 | / |
| Fibrin (F) | 16.680 | / |
| thrombin(t) | 18.778 | / |
| thrombin + fibrin (t + F) | 12.582 | 18.578 |
| TNHH + fibrin (T + F) | 14.598 | / |
| TNHH + thrombin + fibrin (T + F + t) | 10.265 | 12.772 |

Result analysis: The retention time of TNHH, fibrin and thrombin was different in the SEP-HPLC, being 23.657, 16.680 and 18.778 min respectively, so they could be effectively separated. The retention time of partially bound thrombin-fibrin was 12.582 min; the retention time of effectively bound TNHH-fibrin was around 14.598 min; and the retention time of bound TNHH, fibrin and thrombin was 10.265 min.

3. Conclusions

The retention time of TNHH, human fibrin and human thrombin was different in the SEP-HPLC. Under the test conditions, their mixture showed the obvious protein peaks with higher molecular weight. Fibrin could bind with thrombin, and TNHH of present invention could bind with fibrin and thrombin. The results showed that TNHH could bind with fibrin and thrombin in vitro, suggesting that hirugen, which was contained in the TNHH and bound with fibrin and thrombin, retained its spatial conformation.

Example 12

In Vitro Test for Reversible Reaction of TNHH and Thrombin

1. Test Materials
1.1 Medicaments

TNHH (3.0 mg/ml); thrombin (127 Unit/ampoule, National Institute for the Control of Pharmaceutical and Biological Products, Lot No.: 20021105); IMUBIND® Hirudin ELISA (American Diagnostica inc. Product No. 853).

1.2 Instruments

Electrothermal thermostatic water bath (XMTB/H-3000 Shanghai Instrument Group Co., Ltd.); Universal Microplate Reader (Elx-800, BIO-TEK INSTRUMENTS INC.); Centrifuger (TGL-16B ShangHai Anting Scientific Instrument Factory).

2. Test Methods

Adding 1.27 ml water into one ampoule of human thrombin, and mixing to obtain 100 Unit/ml solution; diluting the mother liquid of TNHH with water to 1.0 mg/ml, taking 0.5 ml thus obtained solution and adding 0.1 ml thrombin solution (50 units of thrombin), reacting at 37 for 2 hr, centrifuging and collecting the supernatant, diluting for 10 times with the dilution solution (taught by the instruction of IMUBIND® Hirudin ELISA Kit), repeating the dilution for 6 times at a four fold gradient, detecting according to the instruction of IMUBIND® Hirudin ELISA Kit, and determining the absorbance at 450 nm wavelength.

3. Test Results and Discussions

None samples were colored, and the positively labeled hirudin (contained in the kit) had a linear relationship. The results showed that the in vitro interaction between TNHH and thrombin was irreversible. Hirudin ELISA Kit was an ELISA kit for specifically binding with the C peptide of hirudin and determining its concentration (See instruction appendix) with a detection limit of 0.1 ng/ml. According to the knowledge of Angiomax (bivalent hirudin), the peptide linkage between PG in the structure of D-FPRP-4×Gly (SEQ ID No: 20)-Hirugen could be hydrolyzed by thrombin, and a C-terminal peptide segment comprising hirugen was released. The above tests indicated that the structure of "FPRP-GSGG (SEQ ID No: 21)-hirugen" within TNHH of present invention could not be hydrolyzed by thrombin, and the combination was irreversible.

Example 13

In Vitro Antiplatelet Aggregation Assay

1 Test Materials
1.1 Medicaments

TNHH (6.0 mg/ml); Human thrombin (127 Unit/ampoule, Lot No.: 20021105, National Institute for the Control of Pharmaceutical and Biological Products). Mannitol injection solution (20% mannitol), Beijing Double-crane Pharmaceutical Co., Ltd. Recombinant hirudin (1.0 mg/ampoule), Lot No.: 20050301, stored at −20, Fujin Biology and Medicine Company.

1.2 Animals

Healthy male Japanese Giant Ear White Rabbits, body weight 2.32±0.21 kg, provided by Animal Center, Third Military Medical University.

1.3 Instruments

Platelet aggregation recorder, BS634 Type, Beijing Biochemical Instruments Factory 2. Experiment Methods Platelet aggregation rate was determined by puncture of the central artery of the ear before administration, and then rabbits were randomly divided into 5 groups (4 in each group) based on the platelet aggregation rate and body weight: (1) negative control group (5.12 mg mannitol/kg), (2) high dose TNHH group (4.0 mg/kg), (3) middle dose TNHH group (2.0 mg/kg), (4) low dose TNHH group (1.0 mg/kg), and (5) positive control group (0.1 mg recombinant hirudin/kg). The rabbits in each group were administered at the dose respectively via intravenous injection from the marginal ear vein. Blood samples were collected at the time of 15 min after administration (timed by stopwatch) by puncture of the central artery of the ear to determine the platelet aggregation rate. The method of platelet aggregation rate determination was described as follows: the blood samples were collected by puncture of the central artery of the ear using silicified syringe. 3.8% anticoagulant sodium citrate solution (blood:anticoagulant=9:1) was used. The sample was centrifuged at 200×g for 8 min, and the supernatant obtained was platelet-rich plasma (PRP); then the remaining part was centrifuged again at 2200×g for 10 min, and the supernatant obtained was platelet-poor plasma (PPP). The platelet in PRP was counted as approximate $4.0 \times 10^5/mm^3$. According to Born's turbidimetry, a turbidimetric tube with 200 μl PRP and a small magnetic bar was placed in a platelet aggregation instrument and incubated at 37 for 1 min. After calibrating with PPP, the platelet was induced to aggregate by adding inductive human thrombin (0.76 IU/ml) under stirring. The effect of medicaments on the aggregation of platelet was analyzed using the aggregation curve and the maximum aggregation rate obtained from the instrument. The maximum aggregation rate was calculated according to the formula below:

$$\text{Maximum aggregation rate} = \frac{PRP \text{ transmittance after aggregation} - PRP \text{ transmittance before agrregation}}{PPP \text{ transmittance} - PRP \text{ transmittance before agrregation}} \times 100\%$$

3. Test Results

TABLE 8

Effect of TNHH on platelet aggregation in rabbits

| Groups | Dose (mg/kg) | Rabbits | aggregation ratio (%, $\bar{x} \pm SD$) | | |
|---|---|---|---|---|---|
| | | | Before administration | 15 min after administration | difference |
| mannitol | / | 4 | 58.13 ± 9.61 | 60.51 ± 9.18 | 2.38 ± 7.04 |
| High dose | 4.0 | 4 | 59.23 ± 6.30 | 9.22 ± 4.51 | 50.92 ± 4.33* |
| Middle dose | 2.0 | 4 | 59.62 ± 7.22 | 19.33 ± 10.25 | 30.30 ± 9.92* |

TABLE 8-continued

Effect of TNHH on platelet aggregation in rabbits

| | | | aggregation ratio (%, $\bar{x} \pm SD$) | | |
|---|---|---|---|---|---|
| Groups | Dose (mg/kg) | Rabbits | Before administration | 15 min after administration | difference |
| Small dose | 1.0 | 4 | 57.19 ± 4.42 | 36.27 ± 12.13 | 20.82 ± 7.98* |
| hirudin | 0.1 | 4 | 58.44 ± 4.42 | 4.34 ± 6.88 | 54.09 ± 8.69* |

*compared with control group (mannitol) P < 0.01

The determination results showed that there was no significant difference among groups before administration in the rabbits with thrombin-induced platelet aggregation. At the time of 15 min after administration, the platelet aggregation ratios in the treatment group and the positive control group were significant lower than those of the negative control group (P<0.01) with obvious dose-dependent effect.

4. Conclusions

The results showed that all of the three doses of TNHH could significantly decrease the platelet aggregation ratio in the rabbit induced by thrombin (P<0.01) at the time of 15 min after administration via intravenous injection from the marginal ear vein of the rabbit. It was suggested that TNHH exhibited the efficacy of inhibiting platelet aggregation, while its efficacy was significant lower than that of positive control of hirudin.

Example 14

Assay on Inhibition of $H_2O_2$ Release from Human Peripheral Blood Leukocyte

1. Test Materials 1.1 Preparation of Human Peripheral Blood Leukocyte 10 ml venous blood was taken from healthy people, and heparin sodium was added for anticoagulation. 10 ml HAS buffer (comprising RPMI 1640+10 mM HEPES+1.2 mM $CaCl_2$+1.0 mM $MgCl_2$+1% HAS, pH 7.4) was added into the blood and mixed. Leukocyte separation solution (Sangon) was charged into a sterile centrifuge tube, and whole blood mixture of the same volume was added slowly, and then centrifuged at 2000 rpm for 15 min. Leukocyte solution was taken from the interface and appropriate 1640 culture medium was added, centrifuged for 10 min, and washed twice. The supernatant was discarded, and appropriate HAS Buffer was added for resuspending the precipitate so as to prepare leukocyte suspension. The cell density was counted and adjusted to $4 \times 10^7$/ml. The product was separated at 37° C. and used within an hour.

1.2 Medicaments and Reagents

TNHH (1.0 mg/ml, titer against leukocyte adhesion 720 unit/ml); horseradish peroxidase (100 unit/mg), purchased from Shanghai Sangon. FMLP (5 mg/ampoule, F3506), Sigma Company; $H_2O_2$ purchased from Chongqing Dongshi Chemical Co., Ltd.; buffer solution for release assay was Hank's solution comprising 25 mM glucose, 10% fetal bovine serum, 200 mg/ml phenol red, 32 mg/ml horseradish peroxidase.

1.3 Instruments

Universal Microplate Reader (Elx-800, BIO-TEK INSTRUMENTS INC.); centrifuger (TGL-16B ShangHai Anting Scientific Instrument Factory).

2. Test Methods

Coating the 24-well plate with Hank's solution comprising 50% fetal bovine serum and culturing at 37 for 60 min; washing the plate with 0.15 M NaCl twice; diluting the cells to $6.0 \times 10^6$/ml with the buffer solution for release assay, adding cells, and culturing at 37 for 5 min; adding FMLP to the final concentration of 250 nM; adding TNHH samples at different concentrations and culturing at 37 for 60 min; pipetting the cell suspension, centrifuging at 8000×g for 3 min, and collecting the supernatant. Adding the supernatant into multiple-wells of a 96-well ELISA plate, adding 1 N NaOH (25 µl) for stopping the reaction, and determining the OD at 610 nm wavelength. Calculating the $IC_{50}$ value of TNHH for inhibiting $H_2O_2$ release, and using the standard $H_2O_2$ solution as a control.

3. Test Results (See Table 9):

TABLE 9

Assay on inhibition of $H_2O_2$ release from human peripheral blood leukocyte

| TNHH concentration (µg/ml) | Average OD value | Inhibition ratio (%) |
|---|---|---|
| 100 | 0.121 | 81.99 |
| 50 | 0.135 | 79.91 |
| 25 | 0.259 | 61.45 |
| 12.5 | 0.317 | 50.82 |
| 6.25 | 0.402 | 40.17 |
| 3.125 | 0.519 | 22.76 |
| 1.562 | 0.628 | 6.55 |
| 0.781 | 0.681 | −1.3 |
| control | 0.672 | |

$H_2O_2$ inhibition ratio = (control OD value − sample OD value)/control OD value × 100%

4. Conclusions

The results in the table 9 showed that the $IC_{50}$ value of TNHH for inhibiting $H_2O_2$ release from human peripheral blood leukocyte was 8.5 µg/ml. It was suggested that TNHH could inhibit the $H_2O_2$ release from human peripheral blood leukocyte, and the inhibition ratio was about 70% compared with the control group. It was demonstrated that the TNHH could inhibit the activation of peripheral leukocyte in addition to inhibiting leukocyte adhesion.

Example 15

In Vitro Whole Blood Anticoagulation Assay

1. Test Materials 1.1 Medicaments

TNHH; heparin sodium, Shanghai Sangon; phosphate buffer solution (10 mmol/L PB, 0.15 mol/L NaCl, pH 7.4).

1.2 Animals

Healthy white rabbit, body weight 2.49 kg.

1.3 Instruments

One rabbit fixation box, two 10 ml injectors, one tube bracket, six tubes, 1 ml pipette and pipette tips.

2. Test Methods and Results 2.1 Sample Dilution

TNHH was diluted to 4 mg/ml, 2 mg/ml, 1 mg/ml, 0.5 mg/ml respectively with phosphate buffer solution (10 mmol/L PB, 0.15 mol/L NaCl, pH7.4). Heparin sodium was prepared to 1 mg/ml with the same buffer solution.

2.2 Test Method

Venous blood was taken from marginal ear vein of the rabbit, and rapidly added into 0#-5# tubes. 0.2 ml of the diluted TNHH samples with different concentrations was added into the 1#-4# tubes, respectively. 0.2 ml phosphate buffer solution was added into the 0# tube, which was used as a negative control. 0.2 ml heparin sodium (1 mg/ml) was added into the 5# tube, which was used as a positive control. The reagents were mixed rapidly and stored at room temperature for 15 min for observing the results.

3. Results (Table 10)

TABLE 10

Assay on the in vitro effects of TNHH on blood anticoagulation

| | 0# tube negative control | 1# tube 0.5 mg/ml | 2# tube 1 mg/ml | 3# tube 2 mg/ml | 4# tube 4 mg/ml | 5# tube positive control |
|---|---|---|---|---|---|---|
| Rabbit blood (ml) | 1.0 | 1.0 | 1.0 | 1.0 | 1.0 | 1.0 |
| TNHH (ml) | / | 0.2 | 0.2 | 0.2 | 0.2 | / |
| Phosphate buffer solution (ml) | 0.2 | / | / | / | / | / |
| heparin sodium (ml) | / | / | / | / | / | 0.2 |
| Test results | coagulated | coagulated | coagulated | coagulated | coagulated | Non-coagulated |

4. Conclusions

In the phosphate buffer solution (negative control), blood was coagulated, and in the heparin sodium (positive control), blood was not coagulated. In the different concentrations of TNHH, blood was coagulated. The results showed that TNHH had no whole blood anticoagulation effects in vitro.

Example 16

Effects of TNHH on the Blood Coagulation System in New Zealand Rabbit

1. Experimental Materials 1.1 Test Medicaments 1.1.1 Name: TNHH

Preparation method: dissolving and diluting to the desired concentration with 0.9% sodium chloride injection solution 1.1.2 Name: Bivalrudin (manufactured by Chengdu Jiexun Biotechnical Co., Ltd.)

Character: lyophilized powder for injection

Specification: 1.0 mg/bottle

Lot No.: 20071001

Storage method: keeping in a dark place at a low-temperature (2-8)

Preparation method: dissolving and diluting to the desired concentration with 0.9% sodium chloride injection solution 1.1.3 Name: Hirudin (Shandong Ahua Biopharmaceutical Co., Ltd.)

Character: lyophilized powder for injection

Specification: 2.0 mg/bottle

Lot No.: 20070510

Storage method: keeping in a dark place at a low-temperature (2~8)

Preparation method: dissolving and diluting to the desired concentration with 0.9% sodium chloride injection solution 2.2 Experimental Animals New Zealand rabbit, provided by Third Military Medical University (Animal Center, Daping Hospital); Certificate No. of experimental animal: SCXK2002-008, male or female, body weight 2.5~3.0 kg. Normal animal breeding conditions (temperature 20-25; relative humidity 40-70%; day and night alternative time 10/14).

2.3 Main Experimental Reagents

Reagent for determining activated partial thromboplastin time (APTT): France SAGO company: Lot No.: 061982;

Reagent for determining prothrombin time (PT): France SAGO company: Lot No.: 061933;

Reagent for determining thrombin time (TT): France SAGO company: Lot No.: 060201;

Sodium citrate anticoagulation tube: Hubei Jinxing Science & Technology Development Co., Ltd., Lot No.: 070208

2.4 Experimental Instruments

Full Automatic Coagulation Analyzer, France DIAGNOSTICA STAGO Co., Ltd., Type: STA.

3. Experimental Methods 3.1 Effect of TNHH on Blood Coagulation System of New Zealand Rabbits In Vivo 24 New Zealand rabbits were randomly divided into four groups: (1) TNHH 6.75 mg/kg group; (2) TNHH 3.375 mg/kg group; (3) bivalrudin 1.5 mg/kg group; and (4) hirudin 0.5 mg/kg group. Medicaments were administrated via intravenous injection from marginal ear vein, and 1.8 ml blood was harvested from marginal ear veins at the time of before administration (0 min), and 10 min, 30 min, 60 min, 120 min and 240 min after administration, respectively (the time for injecting is 2 min). 3.2% sodium citrate (9:1) was added for anticoagulation and then mixed and centrifuged at 3000 rpm/min for 3 min. The plasma was send to Department of Clinical Laboratory, Southwest Hospital for determining blood coagulation indexes (APTT, TT and PT) with a full automatic coagulation analyzer and the difference before and after administration was obtained by comparison.

3.2 Effects of TNHH on Blood Coagulation System of New Zealand Rabbits In Vitro

Medicaments were diluted to the following concentrations for use: TNHH: 3.0 mg/ml; 1.0 mg/ml; 333 µg/ml; bivalrudin: 600 µg/ml; 200 µg/ml; 67 µg/ml; Hirudin: 660 µg/ml; 220 µg/ml; 73 µg/ml.

The blood was sampled from six New Zealand rabbits (10×1.8 ml for each one) from marginal ear vein and added into 10 anticoagulation tubes, respectively. 3.2% sodium citrate (9:1) was added for anticoagulation.

20 µl anticoagulated blood was taken from each tube, followed by the addition of 20 µl above diluted medicaments for each tube. 20 µl physiological saline was added into the control tube. Samples were mixed thoroughly and centrifuged at 3000 rpm/min for 3 min, and plasma was send to Department of Clinical Laboratory, Southwest Hospital for determining blood coagulation indexes (APTT, TT and PT) with a full automatic coagulation analyzer and the difference before and after administration was obtained by comparison.

4. Statistical Analysis

SPSS 13.0 software was used for statistical analysis. The experimental results are represented by (x̄±s). Single factor analysis of variance was used for the inter-group comparison. p<0.05 means significant difference, and p<0.01 means very significant difference.

5. Experimental Results 5.1 Effects of TNHH on Blood Coagulation System of New Zealand Rabbits In Vivo 5.1.1 Changes of APTT Changes of APTT at different doses of TNHH and different blood sampling time were shown on table 11.

The results in the table 11 showed that compared with the 0 min control group, there was no obvious extension for APTT in the 3.375 mg/kg TNHH group and the 6.675 mg/kg TNHH group at 10 min, 30 min, 60 min, 120 min and 240 min after administration (P>0.05), which suggested that none of above TNHH doses had obvious effects on APTT within 4 hours.

Similarly, there was no obvious extension for APTT in the bivalrudin 1.5 mg/kg group and the hirudin 0.5 mg/kg group at 10 min, 30 min, 60 min, 120 min and 240 min after administration (P>0.05).

TABLE 11

Effects of TNHH on APTT in rabbits at different time (x ± s, n = 6)

| time | TNHH (mg/kg) | | Bivalrudin (mg/kg) | Hirudin (mg/kg) |
|---|---|---|---|---|
| (min) | 3.375 | 6.675 | 1.50 | 0.50 |
| 0 | 36.45 ± 6.60 | 44.25 ± 5.39 | 40.7 ± 5.77 | 38.02 ± 6.54 |
| 10 | 37.38 ± 6.35 | 39.87 ± 4.98 | 45.75 ± 7.20 | 39.97 ± 5.69 |
| 30 | 31.97 ± 2.11 | 37.98 ± 4.77 | 39.33 ± 6.62 | 37.72 ± 5.55 |
| 60 | 31.93 ± 2.39 | 36.17 ± 6.76 | 38.03 ± 5.55 | 35.02 ± 7.59 |
| 120 | 30.52 ± 6.86 | 38.95 ± 8.85 | 32.68 ± 4.77* | 32.05 ± 5.69 |
| 240 | 35.65 ± 9.36 | 38.03 ± 9.11 | 34.57 ± 5.56 | 32.07 ± 5.97 |

(*P < 0.05 vs 0 min; non-labeled: P > 0.05 vs 0 min)

5.1.2 Plasma Prothrombin Time (PT)

Changes of PT at different doses of TNHH and different blood sampling time were shown on table 12.

The results in the table 12 showed that compared with the 0 min control group, there was no obvious extension for PT in the 3.375 mg/kg TNHH group at 10 min, 30 min, 60 min, 120 min and 240 min after administration (P>0.05), while there was obvious extension for PT in the 6.675 mg/kg TNHH group at 120 min and 240 min after administration (P<0.05). The extension time in the 6.675 mg/kg TNHH group was less than 3 seconds, which had no clinical significance. It was suggested that a low dose of TNHH (3.375 mg/kg) had no significant effects on PT, while a high dose of TNHH (6.675 mg/kg) had certain effects on PT, but making no clinical significance.

There was significant extension for PT in the bivalrudin (1.5 mg/kg) group at 10 min and 30 min (P<0.05) and in the hirudin (0.5 mg/kg) group at 10 min (P<0.05). However, the extension time was less than 3 seconds, thus having no clinical significance.

TABLE 12

Effects of i.v. TNHH on PT in rabbits at different time (x ± s, n = 6)

| time | TNHH (mg/kg) | | Bivalrudin (mg/kg) | Hirudin (mg/kg) |
|---|---|---|---|---|
| (min) | 3.375 | 6.675 | 1.50 | 0.50 |
| 0 | 6.78 ± 0.28 | 6.88 ± 0.17 | 6.87 ± 0.21 | 6.80 ± 0.28 |
| 10 | 6.90 ± 0.21 | 7.17 ± 0.36 | 8.27 ± 0.67* | 7.27 ± 0.22* |
| 30 | 6.85 ± 0.23 | 7.12 ± 0.47 | 7.40 ± 0.27* | 7.01 ± 0.31 |
| 60 | 6.78 ± 0.22 | 7.17 ± 0.40 | 7.10 ± 0.15 | 6.95 ± 0.34 |
| 120 | 6.87 ± 0.32 | 7.62 ± 0.64* | 7.02 ± 0.12 | 6.97 ± 0.27 |
| 240 | 7.02 ± 0.24 | 7.97 ± 0.99* | 6.90 ± 0.18 | 7.08 ± 0.26 |

(*P < 0.05 vs 0 min; non-labeled: P > 0.05 vs 0 min)

5.1.3 Plasma Thrombin Time (TT)

Changes of TT at different doses of TNHH and different blood sampling time were shown on table 13.

The results in the table 13 showed that compared with the 0 min control group, there was obvious extension for TT in the 3.375 mg/kg TNHH group at 10 min after administration (P<0.05), while there was no obvious extension for the sampling time at or later than 20 min after administration. There was obvious extension for TT in the 6.675 mg/kg TNHH group at 10 min and 30 min after administration (P<0.05). It was suggested that a low dose of TNHH (3.375 mg/kg) had a short effects on TT, while a high dose of TNHH (6.675 mg/kg) had certain effects on TT.

There was significant extension for TT in the 1.5 mg/kg bivalrudin group at 10 min and 30 min (P<0.01) and in the 0.5 mg/kg hirudin group at 10 min, 30 min and 60 min (P<0.01).

TABLE 13

Effects of TNHH on TT in rabbits at different time (x ± s, n = 6)

| time | TNHH (mg/kg) | | Bivalrudin (mg/kg) | Hirudin (mg/kg) |
|---|---|---|---|---|
| (min) | 3.375 | 6.675 | 1.50 | 0.50 |
| 0 | 15.57 ± 1.09 | 15.97 ± 1.42 | 15.28 ± 1.60 | 16.40 ± 1.73 |
| 10 | 23.23 ± 2.47* | 33.57 ± 4.47* | 71.18 ± 23.37# | 112.70 ± 38.55# |
| 30 | 16.13 ± 1.31 | 21.63 ± 1.71* | 36.12 ± 14.00# | 84.93 ± 49.24# |
| 60 | 14.75 ± 1.44 | 15.55 ± 0.95 | 26.68 ± 7.30 | 58.17 ± 33.19# |
| 120 | 14.02 ± 0.79 | 15.00 ± 1.51 | 15.40 ± 2.16 | 30.42 ± 17.09 |
| 240 | 14.65 ± 1.14 | 13.33 ± 0.73* | 15.50 ± 2.36 | 16.30 ± 2.32 |

(*P < 0.05 vs 0 min; #P < 0.01 vs 0 min; non-labeled: P > 0.05 vs 0 min)

5.2 Effects of TNHH on Blood Coagulation System of New Zealand Rabbits In Vitro

The results in the table 14 showed that compared with the control group, there was no significant difference for APTT and PT in low, middle and high dose TNHH groups (P>0.05), and there was obvious extension for TT only in the high dose (30 μg/ml) TNHH group (P<0.05).

There was obvious extension for APTT, PT and TT only in the high dose (6 μg/ml) bivalrudin group. In the 2 μg/ml and 0.67 μg/ml bivalrudin groups, there was no obvious extension for APTT (P>0.05), while there was obvious extension for TT (2 μg/ml bivalrudin, P<0.05; 0.67 μg/ml bivalrudin, P<0.01) and PT (P<0.05). However, the extension time of PT was less than 3 seconds, thus having no clinical significance. There was obvious extension for APTT, PT and TT in the 6.6 μg/ml and 2.2 μg/ml hirudin groups (P<0.05), however, the extension time of PT was less than 3 seconds thus having no clinical significance. In the 0.73 μg/ml hirudin groups, there was no obvious extension for APTT and PT (P>0.05), while there was obvious extension for TT (P<0.01).

TABLE 14

Effects of TNHH on in vitro blood coagulation system in New Zealand rabbit (x ± s, n = 6)

| Groups (μg/ml) | | APTT | PT | TT |
|---|---|---|---|---|
| Control group (20 μl NS) | | 34.28 ± 4.58 | 7.08 ± 0.27 | 15.50 ± 1.83 |
| TNHH | 30.00 | 38.08 ± 5.53 | 7.27 ± 0.38 | 30.00 ± 4.81* |
| | 10.00 | 31.87 ± 4.46 | 7.15 ± 0.24 | 20.43 ± 1.59 |
| | 3.33 | 33.73 ± 6.35 | 7.08 ± 0.28 | 17.13 ± 1.46 |
| bivalrudin | 6.00 | 55.00 ± 12.4* | 11.08 ± 1.20* | 85.38 ± 23.07# |
| | 2.00 | 40.75 ± 8.71 | 8.75 ± 0.52* | 53.67 ± 9.03# |
| | 0.67 | 35.12 ± 8.04 | 7.83 ± 0.39* | 43.22 ± 8.13* |
| hirudin | 6.60 | 58.43 ± 14.36* | 9.37 ± 1.30* | 116.40 ± 8.82# |
| | 2.20 | 52.85 ± 15.88* | 7.87 ± 0.37* | 102.77 ± 21.90# |
| | 0.73 | 37.47 ± 6.15 | 7.33 ± 0.33 | 50.40 ± 8.19# |

(*: P < 0.05 vs Control; #: P < 0.01 vs 0 min; non-labeled: P > 0.05 vs 0 min)

7. Conclusions

In the case that a dose in great excess of the effective dose for experimentally therapeutic acute ischemic brain stroke is administrated, TNHH had no effects on the endogenous blood coagulation pathway, while had some effects on the exogenous blood coagulation pathway and fibrinolytic system.

Example 17

Protective Effects of TNHH on Focal Cerebral Ischemia-Reperfusion Injury in Rats 1. Materials and Instruments 1.1 Medicaments and Reagents (1) Chloral hydrate, China National Medicine Group, Shanghai Chemical Reagent Company (2) TNHH product prepared from Example 5

(3) 2,3,5-Triphenyltetrazolium Chloride, TTC, E. Merck, sub-packaged by Sub-packaging Department, Shanghai Chemical Reagent Company, prepared with PBS, stored in dark at a low temperature.

(4) 25% mannitol, Wuhan Binhu Double-crane pharmaceutical Co., Ltd., Lot No.: 070417-504, diluted to 4% mannitol with 10 mM PB, pH 7.0.

1.2 Experimental Instruments (1) Commercial available 2.5# nylon thread (Made in China), diameter 0.22 mm, 0.24 mm, 0.26 mm.

(2) Medical 4# thread, manufactured from Shanghai Medical sewing needle Factory.

(3) Japanese 1472-CHA Type Electronic Precision Balance (4) Image analytical software system, Chengdu TME 1.3 Experimental Animals Sprague-Dawley (SD) rats, male, clean grade, body weight 180-250 g, provided by Experimental Animal Center, Tongji Medical College of Huazhong University of Science & Technology. Animal certificate No.: SYXK (E) 2004-0029

2. Methods 2.1 Preparation of Focal Cerebral Ischemia Models in Rats

Middle cerebral artery occlusion (MCAO) models (on one side) were established according to Nagasawa method[2] with some modifications. The operation process comprised the following steps: weighting the rats, performing anaesthesia by intraperitoneal injection of 10% chloral hydrate (300 mg·kg$^{-1}$), and fixing the rats on thermostat operation table (37±0.5). The skin of neck was disinfected with iodine alcohol solution, and median skin incision was performed allowing blunt separation of subcutaneous tissues and muscles to avoid of thyroid gland and parathyroid gland being damaged. The common carotid artery on one side and its external carotid artery and internal carotid artery branches were seeked out to the furcation of pterygopalatine artery and then ligating the pterygopalatine artery, internal carotid artery and common carotid artery respectively with threads for later use. A small aperture was opened at the common carotid artery bifurcation, and then a nylon thread with diameter of 0.23-0.26 mm (the diameter selection should be selected according to the weight of animal) was inserted along internal carotid artery towards the intracranial part to anterior cerebral artery with insertion depth of 17-20 mm till it could not move forward encountering resistance. The nylon thread was ligated together with internal carotid artery. The subcutaneous fascia and skin was sutured, and then the middle cerebral artery occlusion-reperfusion model was established when pulling out the suture after 1 h or 2 h occlusion. The operation process in sham operation group was the same as that in the operation group but without vessel occlusion by nylon thread.

2.2 Nervous Symptom Scoring

After the rats got conscious, the nervous symptom changes were observed which exhibited mainly as:

(1) Horner's syndrome: the pupil on the ischemic side shrank, and the eyeball sunk inward, the rima oculi reduced, and the muscular tension enhanced relatively; while the eyeball on the non-ischemic side extruded slightly, and the pupil and rima oculi were normal, and the muscular tension decreased.

(2) Postures: when lifted by the tail, the rats exhibited as forced posture, and the body turned to the non-ischemic side. The forelimb on the non-ischemic side shrank tightly toward the chest, while the forelimb and hind limb on the ischemic side stretched outward.

(3) Tail chasing syndrome: the body rotated towards the non-ischemic side when moved, which was just like chasing its own tail. When the rotation stopped, the tail coiled in a special spiral shape.

Nervous symptom was evaluated based on Longa 5-grade standard[3]. The grading standard was described as follows: no nervous damage symptom: 0; left forepaw could not fully spread: 1; rotating toward the non-ischemic side: 2; falling toward the non-ischemic side during walking: 3; could not walk on its own and lost consciousness: 4.

2.4 TTC Staining

Principle of TTC staining: TTC (2,3,5-triphenyltetrazolium chloride) exists as reduced form (red) and oxidized form (colorless). NADPH in normal brain tissue can reduce colorless TTC in oxidized form into red TTC in reduced form. Cerebral ischemia results in the ischemic necrosis of nerve cells in the infarcted area and the loss of NADPH that is responsible for reducing TTC, and such region of the brain tissue shows an offwhite color. In contrast, the normal brain tissue shows a red color resulting from the presence of NADHP that can reduce an oxidized TTC into a reduced TTC, thus differentiating the ischemia infarction area from the non-ischemic normal brain tissue.

TTC staining method: After 48 h of ischemia-reperfusion, the rats were sacrificed by decapitation. The brains were collected with olfactory bulb, cerebellum and lower brain stem removed, and then freezed at −20 for 10 min. Slicing along the coronal section of optic chiasma to obtain 7 sections (thickness of 2 mm). The sections were placed in 2% TTC solution, incubated in dark at 37 for 30 min, and fixed in the 10% formaldehyde.

2.5 Determination of Cerebral Infarction Volume

Cerebral infarction volume: the sections were orderly arranged and photographed with a digital camera. The photos were then inputted into a computer, analyzed with an analytical software (see methods in the reference[4]) and infarction percentage was calculated. Calculation formula: infarction percentage (%)=area of white color region/total area of whole brain×100%.

2.6 Grouping and Administration

1. Blank control group: No any treatment was taken for animals except for feeding at the same conditions
2. Sham operation group: Taking the same operation process as the model group except for block vessel
3. Model group: Embolization for 1 h-reperfusion for 48 h Ischemia for 2 h-reperfusion for 48 h
4. Rat models were randomly divided into three dose groups:

Ischemia 60 min-reperfusion 2 h group, i.v. administration of TNHH 0.75 mg/kg;
Ischemia 60 min-reperfusion 2 h group, i.v. administration of TNHH 2.25 mg/kg;
Ischemia 60 min-reperfusion 2 h group, i.v. administration of TNHH 6.75 mg/kg;
Ischemia 120 min-reperfusion 2 h group, i.v. administration of TNHH 0.75 mg/kg;
Ischemia 120 min-reperfusion 2 h group, i.v. administration of TNHH 2.25 mg/kg;
Ischemia 120 min-reperfusion 2 h group, i.v. administration of TNHH 6.75 mg/kg 5. Vehicle Control Group Ischemia 60 min-reperfusion 2 h group, i.v. administration of 4% mannitol;
Ischemia 120 min-reperfusion 2 h group, i.v. administration of 4% mannitol Administration method: intravenous injection (2 min), twice per day with at least 8 hour interval: administrating at the time of 2 hours after MCAO reperfusion; administration volume: 0.5 ml/per animal/time Administration time: The first day: administrating at 2 h and 10 h after reperfusion, respectively; the second day: administrating twice per day with 8 hour interval; experimental enduration: sacrificing rats after 48 h of the first administration 2.6 Statistical Analysis Experimental data is presented by mean±S.E.M. Significant difference analysis was performed with one-way ANOVA, post-hoc LSD test and independent-samples T test by SPSS 11.5 software. p<0.05 means significant difference, and p<0.01 means very significant difference.

3. Results 3.1 Effects of TNHH on Symptom of Neural Behavior of MCAO Rat

Significant neural motor dysfunction occurred to the rat occluded for 1 h and reperfused for 48 h. When the rat was lifted by the tail, a tail chasing symptom was observed, including the left forelimb inflected to shrink inward, and the muscular tension of the left limb decreased, and it tended to rotate toward the non-ischemic side during walking. The symptoms were progressively aggravated during observation. The neural symptom scoring was listed as follows: 1.77±0.59 at 2 h; 1.73±0.59 at 6 h; 1.73±0.42 at 12 h; 1.83±0.49 at 24 h; 1.87±0.58 at 48 h. Intravenous injection of TNHH (the dosing and grouping was the same as set above) was performed at 2 h after the reperfusion, and the symptom of animals in various treatment groups was alleviated at various time points, which was especially significant in high dose group with very significant statistical difference (P<0.01) when compared with that in the model group. The neural function symptom of the MACO rats occluded for 2 h and reperfused for 48 h was more severe than the MACO rats occluded for 1 h and reperfused for 48 h. The neural symptom scoring was listed as follows: 1.96±0.75 at 2 h; 2.19±0.69 at 6 h; 2.32±0.82 at 12 h; 2.12±0.79 at 24 h; 2.23±0.69 at 48 h. The neural symptom of the rats treated with TNHH was also significantly improved, and it was more significant in high dose group. The difference was statistically significant (p<0.05) when compared with that in corresponding model group; the neural symptom of rats was not significantly improved by administration of 4% mannitol in the vehicle control group compared with that in model group. The experiment results were listed in table 15.

3.2 Effects of TNHH on Cerebral Infraction Volume in MCAO Reperfusion Rats

After MCAO obstruction 1 h and then reperfusion 48 h, the cerebral infraction volume of rats was (22.281±4.71) %. Intravenous injection of TNHH at 2 h after reperfusion resulted in decreased cerebral infraction volume: low dose group: (19.93±12.40) %; middle dose group: (19.41±11.74) %; and high dose group: (12.89±8.94) %, decreasing by 10.54%, 12.88% and 42.14% respectively, compared with that of the model group. The effect of the high dose group was the most significant compared with that of the model group (P<0.01). After MCAO obstruction 2 h and then reperfusion 48 h, the cerebral infraction volume of rats was (28.16±10.90) %. The treatment with the same dose of TNHH resulted in decreased cerebral infraction volume: low dose group: (27.52±17.63) %; middle dose group: (26.07±8.06) %; and high dose group: (19.72±8.90) %, decreasing by 3.63%, 7.42% and 29.97% respectively, compared with that of the model group. The effect of the high dose group was the most significant compared with that of the model group (P<0.01). 4% mannitol was administrated into the vehicle control group, and it showed no improved effects on the cerebral infraction volume of animals compared with the two model groups. The experimental results were shown on the table 16.

TABLE 15

Effect of TNHH on nervous symptoms after 48 h of acute focal cerebral ischemia-reperfusion in rats ($\bar{x} \pm s$, n = 10)

| Groups | | nervous symptom score (time: h) | | | | |
|---|---|---|---|---|---|---|
| | | 2 | 6 | 12 | 24 | 48 |
| Control Group | | 0 | 0 | 0 | 0 | 0 |
| Sham-operation group | | 0 | 0 | 0 | 0 | 0 |
| M-1 | | 1.77 ± 0.59 | 1.73 ± 0.59 | 1.73 ± 0.42 | 1.83 ± 0.49 | 1.87 ± 0.58 |
| M-2 | | 1.96 ± 0.75 | 2.19 ± 0.69 | 2.32 ± 0.82 | 2.12 ± 0.79 | 2.23 ± 0.69 |
| M-1 | 0.75 mg/kg | 1.46 ± 0.58 | 1.42 ± 0.60 | 1.42 ± 0.60 | 1.40 ± 0.43 | 1.36 ± 0.62 |
| | 2.25 mg/kg | 1.47 ± 0.92 | 1.47 ± 0.92 | 1.37 ± 0.92 | 1.38 ± 0.41 | 1.30 ± 0.76* |
| | 6.75 mg/kg | 1.50 ± 0.58 | 1.50 ± 0.68 | 1.39 ± 0.65* | 1.20 ± 0.36* | 1.00 ± 0.42** |
| M-2 | 0.75 mg/kg | 1.94 ± 0.56 | 1.94 ± 0.56 | 1.94 ± 0.73 | 1.88 ± 0.64 | 1.86 ± 0.77 |
| | 2.25 mg/kg | 1.81 ± 0.92 | 1.80 ± 0.92 | 1.79 ± 0.92 | 1.68 ± 0.41* | 1.67 ± 0.76* |
| | 6.75 mg/kg | 1.75 ± 0.52 | 1.75 ± 0.27 | 1.50 ± 0.45* | 1.37 ± 0.52* | 1.22 ± 0.38** |

TABLE 15-continued

Effect of TNHH on nervous symptoms after 48 h of acute focal cerebral ischemia-reperfusion in rats ($\bar{x} \pm s$, n = 10)

| Groups | nervous symptom score (time: h) | | | | |
|---|---|---|---|---|---|
| | 2 | 6 | 12 | 24 | 48 |
| M-1 + mannitol | 1.49 ± 0.92 | 1.47 ± 0.69 | 1.47 ± 0.77 | 1.50 ± 0.65 | 1.50 ± 0.76 |
| M-2 + mannitol | 1.51 ± 0.98 | 1.49 ± 0.92 | 1.49 ± 0.92 | 1.50 ± 0.41 | 1.58 ± 0.78 |

*Compared with the model groups, P < 0.05; showing significant difference;
**Compared with the model groups, P < 0.01; showing very significant difference P < 0.01

TABLE 16

Effect of TNHH on cerebral infraction volume after 48 h of acute focal cerebral ischemia-reperfusion in rats ($\bar{x} \pm s$, n = 10)

| Groups | Doses (mg/kg) | Cerebral infarction volume (%), based on the total volume of the brain | Decrease in percentage (%), compared with corresponding model group |
|---|---|---|---|
| Blank control group | 0 | | |
| sham operation group | 0 | | |
| M-1 | 0 | 22.28 ± 8.46 | |
| M-2 | 0 | 28.16 ± 10.90 | |
| M-1 | 0.75 | 19.93 ± 12.40 | 10.54 |
| | 2.25 | 19.41 ± 11.74 | 12.88* |
| | 6.75 | 12.89 ± 8.94 | 42.15** |
| M-2 | 0.75 | 27.52 ± 7.63 | 3.63 |
| | 2.25 | 26.07 ± 8.06 | 7.42 |
| | 6.75 | 19.72 ± 5.90 | 29.97** |
| M-1 + 4% mannitol | 0.5 ml | 24.18 ± 9.45 | +8.52 |
| M-2 + 4% mannitol | 0.5 ml | 27.68 ± 10.06 | 1.70 |

*Compared with the model groups, P < 0.05; showing significant difference;
**Compared with the model groups, P < 0.01; showing very significant difference P < 0.01

Although particular embodiments of the invention have been disclosed herein in detail, this has been done by way of example and for the purposes of illustration only, and is not intended to limit the scope of the present invention. It is obvious that various alterations or modifications may be made to the invention in light of the description above. Exhaustive listing of all embodiments is not required and unnecessary. Those obvious alterations or modifications within the spirit of the invention will fall into the scope of the present invention.

We claim:

1. A recombinant chimeric protein of neutrophil inhibitory factor (NIF) and hirugen, comprising:
   (1) the amino acid sequence of Met-NIF-linker 1-FPRP (SEQ ID NO:11)-linker 2-hirugen;
   (2) the amino acid sequence of NIF-linker 1-FPRP(SEQ ID NO:11)-linker 2-hirugen, or
   (3) an amino acid sequence that is greater than 90% identical to the sequence of SEQ ID NO:3, including the amino acid sequence FPRPGSGG (SEQ ID NO:21) wherein the recombinant chimeric protein has an activity of treating cardio-cerebrovascular diseases, the linker 1 being 5-15 glycines and the linker 2 being $(GSGG)_{1-3}$ (SEQ ID NOs:12-14).

2. The recombinant chimeric protein of neutrophil inhibitory factor and hirugen according to claim 1, wherein the phenylalanine (F) in FPRPGSGG (SEQ ID NO:21) is in L-form.

3. The recombinant chimeric protein of neutrophil inhibitory factor and hirugen according to claim 2, wherein the linker 1 is 5 glycines, and the linker 2 is GSGG (SEQ ID NO:12).

4. The recombinant chimeric protein of neutrophil inhibitory factor and hirugen according to claim 2, having the sequence of SEQ ID NO:3.

5. A pharmaceutical composition comprising the recombinant chimeric protein of neutrophil inhibitory factor and hirugen according to claim 1.

6. The pharmaceutical composition according to claim 5, which is in a form for parenteral administration.

7. A method of treating a cardio-cerebrovascular disease, comprising administering to a subject in need thereof the pharmaceutical composition of claim 5.

8. The recombinant chimeric protein of neutrophil inhibitory factor and hirugen according to claim 1, wherein the recombinant chimeric protein inhibits thrombin activity.

9. The pharmaceutical composition of claim 5, wherein the phenylalanine (F) in FPRPGSGG (SEQ ID NO:21) is in L-form.

10. The pharmaceutical composition of claim 9, wherein the linker 1 is 5 glycines, and the linker 2 is GSGG (SEQ ID NO:12).

11. The pharmaceutical composition of claim 9, wherein the recombinant chimeric protein of neutrophil inhibitory factor and hirugen has the sequence of SEQ ID NO:3.

12. The method of claim 7, wherein the cardio-cerebrovascular disease is cerebral ischemic injury.

13. The method of claim 7, wherein the cardio-cerebrovascular disease is cerebral hematoma.

14. The method of claim 7, wherein the cardio-cerebrovascular disease is stroke.

15. The method of claim 7, wherein the phenylalanine (F) in FPRPGSGG (SEQ ID NO:21) is in L-form.

16. The method of claim 15, wherein the linker 1 is 5 glycines, and the linker 2 is GSGG (SEQ ID NO:12).

17. The method of claim 15, wherein the recombinant chimeric protein of neutrophil inhibitory factor and hirugen has the sequence of SEQ ID NO:3.

* * * * *